(12) United States Patent
Vandersarl et al.

(10) Patent No.: US 10,150,947 B2
(45) Date of Patent: *Dec. 11, 2018

(54) NANOTUBE STRUCTURES, METHODS OF MAKING NANOTUBE STRUCTURES, AND METHODS OF ACCESSING INTRACELLULAR SPACE

(71) Applicant: THE BOARD OF TRUSTEES OF THE LELAND STANFORD JUNIOR UNIVERSITY, Stanford, CA (US)

(72) Inventors: Jules J. Vandersarl, Eagle, ID (US); Alexander M. Xu, Stanford, CA (US); Nicholas A. Melosh, Menlo Park, CA (US); Noureddine Tayebi, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/991,853

(22) Filed: Jan. 8, 2016

(65) Prior Publication Data

US 2016/0201030 A1    Jul. 14, 2016

Related U.S. Application Data

(62) Division of application No. 13/455,245, filed on Apr. 25, 2012, now Pat. No. 9,266,725.

(60) Provisional application No. 61/479,423, filed on Apr. 27, 2011, provisional application No. 61/584,421, filed on Jan. 9, 2012.

(51) Int. Cl.
*C12N 5/00* (2006.01)
*B82Y 40/00* (2011.01)
*B82Y 5/00* (2011.01)

(52) U.S. Cl.
CPC ............. *C12N 5/0075* (2013.01); *B82Y 5/00* (2013.01); *B82Y 40/00* (2013.01); *C12N 5/0068* (2013.01); *C12N 2521/00* (2013.01); *C12N 2533/10* (2013.01); *C12N 2533/30* (2013.01); *C12N 2535/00* (2013.01)

(58) Field of Classification Search
None
See application file for complete search history.

(56) References Cited

U.S. PATENT DOCUMENTS

| | | |
|---|---|---|
| 6,368,851 B1 | 4/2002 | Baumann et al. |
| 7,152,616 B2 | 12/2006 | Zucchelli et al. |
| 7,160,532 B2 | 1/2007 | Liu et al. |
| 8,808,516 B2 | 8/2014 | Melosh et al. |
| 9,266,725 B2 | 2/2016 | Vandersarl et al. |
| 2004/0182707 A1 | 9/2004 | Jardemark et al. |
| 2006/0213259 A1 | 9/2006 | Prinz et al. |
| 2007/0100086 A1 | 5/2007 | Hong et al. |
| 2008/0302960 A1 | 12/2008 | Meister et al. |
| 2009/0220561 A1 | 9/2009 | Jin et al. |
| 2010/0035322 A1 | 2/2010 | Raffa et al. |
| 2010/0140111 A1 | 6/2010 | Gimsa et al. |
| 2010/0215724 A1 | 8/2010 | Prakash et al. |
| 2011/0168968 A1 | 7/2011 | Yang et al. |
| 2011/0208031 A1 | 8/2011 | Wolfe et al. |
| 2012/0040370 A1 | 2/2012 | Orwar et al. |
| 2012/0225435 A1 | 9/2012 | Seger et al. |
| 2012/0264108 A1 | 10/2012 | Chen et al. |
| 2013/0118621 A1 | 5/2013 | Weber et al. |
| 2014/0342445 A1 | 11/2014 | Ingber et al. |
| 2014/0353172 A1 | 12/2014 | Melosh et al. |

OTHER PUBLICATIONS

Abhyankar et al.; Characterization of a membrane-based gradient generator for use in cell-signaling studies; Lab Chip; 6(3):389-393; Mar. 2006.
Adler et al.; Emerging links between surface nanotechnology and endocytosis: impact on nonviral gene delivery; Nano Today; 5(6):553-569; Dec. 2010 (author manuscript, 15 pgs.).
Ainslie et al.; Microfabricated devices for enhanced bioadhesive drug delivery: attachment to and small-molecule release through a cell monolayer under flow; Small; 5(24):2857-2863; Dec. 2009.
Almquist et al.; Fusion of biomimetic stealth probes into lipid bilayer cores; Proc Natl Acad Sci U S A.; 107(13):5815-5820; Mar. 2010.
Almquist et al.; Nanoscale patterning controls inorganic-membrane interface structure; Nanoscale; 3(2):391-400; Feb. 2011.
Bancroft et al.; Fluid flow increases mineralized matrix deposition in 3D perfusion culture of marrow stromal osteoblasts in a dose-dependent manner; PNAS; 99(20):12600-12605; Oct. 1, 2002.
Bernards et al.; Nanoscale porosity in polymer films: fabrication and therapeutic applications; Soft Matter; 6(8):1621-1631; Jan. 2010 (author manuscript, 13 pgs.).
Black et al.; Upregulation of a silent sodium channel after peripheral, not not central, nerve injury in DRG neurons; J Neurophysiol; 82(5); pp. 2776-2785; Nov. 1999.
Boyden; The chemotactic effect of mixtures of antibody and antigen on polymorphonuclear leucocytes; J Exp Med; 115:453-466; Mar. 1, 1962.
Cao et al.; Template-based synthesis of nanorods, nanowire and nanotube array; Adv Colloid Interface Sci; 136(1-2):45-64; Jan. 15, 2008.
Carter; Potent antibody therapeutics by design; Nat Rev Immunol; 6 (5):343-57; May 2006.
Chen et al.; A cell nanoinjector based on carbon nanotubes; Proc Natl Acad Sci U S A.; 104(20):8218-8222; May 15, 2007.
Choi; A Cellular Trojan Horse for Delivery of Therapeutic Nanoparticles into Tumors. Nano Letters; 7(12), pp. 3759-3765; Dec. 2007.

(Continued)

*Primary Examiner* — Renee Claytor
*Assistant Examiner* — Srikanth Patury
(74) *Attorney, Agent, or Firm* — Shay Glenn LLP

(57) ABSTRACT

In accordance with the purpose(s) of the present disclosure, as embodied and broadly described herein, embodiments of the present disclosure, in one aspect, relate to methods of making a structure including nanotubes, a structure including nanotubes, methods of delivering a fluid to a cell, methods of removing a fluid to a cell, methods of accessing intracellular space, and the like.

18 Claims, 20 Drawing Sheets

(56) References Cited

OTHER PUBLICATIONS

Chu et al.; Electroporation for the efficient transfection of mammalian cells with DNA; Nucleic Acids Res.; 15(3):1311-1326; Feb. 11, 1987.
Daub et al.; Ferromagnetic nanotubes by atomic layer deposition in anodic alumina membranes; J. Appl. Phys.; 101; 09J111 (4 pgs.); May 2007.
Dertinger et al.; Generation of Gradients Having Complex Shapes Using Microfluidic Networks; Anal Chem; 73:1240-1246; Feb. 16, 2001.
Diao et al.; A three-channel microfluidic device for generating static linear gradients and its application to the quantitative analysis of bacterial chemotaxis; Lab Chip; 6(3):381-388; Mar. 2006.
Dubey et al.; Intercellular nanotubes mediate bacterial communication; Cell; 144(4):590-600; Feb. 2011.
El-Ali et al.; Cells on Chips; Nature; 442(7101):403-411; Jul. 27, 2006.
Engler et al.; Matrix Elasticity Directs Stem Cell Lineage Specification; Cell; 126(4):677-689; Aug. 25, 2006.
Ertan et al.; Electrodeposition of nickel nanowires and nanotubes using various templates; Journal of Experimental Nanoscience; 3 (4); pp. 287-295; Dec. 2008.
Gasiorowski et al.; Alterations in gene expression of human vascular endothelial cells associated with nanotopographic cues; Biomaterials; 31(34):8882-8; Dec. 2010 (author manuscript, 15 pgs.).
Geldof; Nerve-growth-factor-dependent neurite outgrowth assay; a research model for chemotherapy-induced neuropathy; J Cancer Res Clin Oncol; 121(11):657-660; Feb. 1995.
Gheith et al; Stimulation of Neural Cells by Lateral Currents in Conductive Layer-by-Layer Films of Single-Walled Carbon Nanotubes; Adv Mater; 18(22):2975-2979; Nov. 2006.
Giancotti et al.; Integrin signaling; Science; 285(5430):1028-1032; Aug. 13, 1999.
Goetz et al; Computer simulations of bilayer membranes: Self-assembly and interfacial tension; J Chem Phys; 108(7):7397-7409; May 1, 1998.
Griffith et al.; Polymeric biomaterials; Acta Mater; 48(1):263-277; Jan. 1, 2000.
Hanna et al.; Direct cell reprogramming is a stochastic process amenable to acceleration; Nature;462(7273):595-601; Dec. 2009 (auhor manuscript, 17 pgs.).
Haydon et al.; Anaesthesia by the n-alkanes. A comparative study of nerve impulse blockage and the properties of black lipid bilayer membranes; BBA-Biomembranes; 470(1):17-34; Oct 3, 1977.
Haydon et al.; The molecular mechanisms of anaesthesia; Nature; 268:356-358; Jul. 28, 1977.
Heath et al.; Nanotechnology and cancer; Annu Rev Med; 59:251-65; Feb. 2008 (author manuscript, 16 pgs.).
James et al.; Patterned protein layers on solid substrates by thin stamp microcontact printing; Langmuir; 14(4); pp. 741-744; Jan. 1998.
Jeon et al.; Generation of Solution and Surface Gradients Using Microfluidic Systems; Langmuir; 16(22):8311-8316; Oct. 31, 2000.
Keenan et al.; Microfluidic fjetsf for generating steady-state gradients of soluble molecules on open surfaces; Appl. Phys. Lett.; 89(11);114103-114103-3; Sep. 11, 2006.
Keenan et al.; Biomolecular gradients in cell culture systems; Lab Chip; 8 (1):34-57; Jan. 2008.
Kim et al.; Interfacing Silicon Nanowires with Mammalian Cells; J Am Chem Soc; 129(23):7228-7229; Jun. 13, 2007.
Kinoshita; Electrochemical Uses of Carbon; Electrochem Encycl; pp. 11; Jan. 2001.
Knez et al.; Synthesis and Surface Engineering of Complex Nanostructures by Atomic Layer Deposition; Adv Mater; 19(21):3425-3437; Nov. 2007.
Kubota et al.; Role of laminin and basement membrane in the morphological differentiation of human endothelial cells into capillary-like structures; Journal of Cell Biology; 107; pp. 1589-1598; Oct. 1988.
Kumar et al.; The gap junction communication channel; Cell; 84(3):381-8; Feb 1996.
Langer; Drug delivery and targeting; Nature; 392(6679 Suppl):5-10.; Apr. 1998.
Langille et al.; Relationship between blood flow direction and endothelial cell orientation at arterial branch sites in rabbits and mice; Circ Res; 48(4):481-488; Apr. 1981.
Lee et al.; Hydrogels for tissue engineering; Chem Rev; 101(7):1869-1879; Jul. 2001.
Li et al.; Nanotube arrays in porous anodic alumina membranes; J. Mater. Sci. Tech.; 24(4); pp. 550-562; Jul. 2008.
Loh et al.; Nanofountain-probe-based high-resolution patterning and single-cell injection of functionalized nanodiamonds; Small; 5(14):1667-1674; Jul. 2009.
Luo et al.; Synthetic DNA delivery systems; Nat Biotechnol; 18(1):33-7; Jan. 2000.
Lutolf et al.; Synthetic biomaterials as instructive extracellular microenvironments for morphogenesis in tissue engineering; Nat Biotecnol; 23(1):47-55; Jan. 2005.
Malboubi et al.; Effects of the Surface Morphology of Pipette Tip on Giga-seal Formation. Engineering Letters; 17(4), p. 281; Nov. 2009.
Martin; Nanomaterials: a membrane-based synthetic approach; Science; 266 (5193):1961-6.; Dec. 1994.
McKnight et al.; Tracking gene expression after DNA delivery using spatially indexed nanofiber arrays; Nano Letters; 4(7); pp. 1213-1219; May 2004.
Michalet et al.; Quantum dots for live cells, in vivo imaging, and diagnostics; Science; 307(5709):538-44; Jan. 28, 2005 (author manuscript; 16 pgs.).
Patel, et al.; Spatially controlled cell engineering on biodegradable polymer surfaces; FASEB J; 12(14):1447-1454; Nov. 1998.
Peng et al.; Whole genome expression analysis reveals differential effects of TiO2 nanotubes on vascular cells; Nano Letters; 10(1); pp. 143-148; Jan. 2010.
Persson et al.; Vertical Nanotubes Connected by a Subsurface Nanochannel; 14th Int'l Conference on Miniturized Systems fror Chemistry and Life Sciences; 1862-1864; Oct. 3-7, 2010.
Petronilli et al.; Transient and long-lasting openings of the mitochondrial permeability transition pore can be monitored directly in intact cells by changes in mitochondrial calcein fluorescence; Biophys J.; 76(2):725-34.; Feb. 1999.
Plath et al.; Progress in understanding reprogramming to the induced pluripotent state; Nat Rev Genet.; 12(4):253-265; Apr. 2011 (author manuscript, 26 pgs.).
Qi; Cell adhesion and spreading behavior on vertically aligned silicon nanowire arrays; ACS Appl Mater Interfaces; 1(1):30-4; Jan. 2009.
Ruoslahti; New perspectives in cell adhesion: RGD and integrins; Science; 238(4826):491-7; Oct. 1987.
Safran et al.; Database update: GeneCards version 3: the human gene integrator; Database (Oxford); vol. 2010 (baq020); 16 pgs.; Aug. 2010.
Saito; A Theoretical Study on the Diffusion Current at the Stationary Electrodes of Circular and Narrow Band Types; Rev Polarography; 15(6):177-187; Dec. 1968.
Sakiyama-Elbert et al.; Controlled release of nerve growth factor from a heparin-containing fibrin-based cell ingrowth matrix; J Control Release; 69(1):149-158; Oct. 3, 2000.
Scadden; The stem-cell niche as an entity of action; Nature; 441 (7097):1075-1079; Jun. 29, 2006.
Shalek et al.; Vertical silicon nanowires as a universal platform for delivering biomolecules into living cells; Proc Natl Acad Sci U S A.; 107(5):1870-1875; Feb. 2, 2010.
Shamloo et al.; Endothelial cell polarization and chemotaxis in a microfluidic device; Lab Chip; 8(8):1292-1299; Aug. 2008.
Susin et al.; Molecular characterization of mitochondrial apoptosis-inducing factor; Nature; 397; pp. 441-446; Feb. 1999.
Tian et al.; Fabrication of high density metallic nanowires and nanotubes for cell culture studies; Microelectronic Eng; 88(8):1702-1706; Aug. 2011.

(56) References Cited

OTHER PUBLICATIONS

Tian et al.; Three-dimensional, flexible nanoscale field-effect transistors as localized bioprobes; Science;329(5993):830-4; Aug. 2010 (author manuscript, 11 pgs.).

Tiscornia et al.; A general method for gene knockdown in mice by using lentiviral vectors expressing small interfering RNA; Proc Natl Acad Sci U S A.; 100(4):1844-1848; Feb. 18, 2003.

Uhrich et al.; Polymer systems for controlled drug release; Chem Rev; 99 (11):3181-3198; Nov. 10, 1999.

Verma et al.; Gigaohm resistance membrane seals with stealth probe electrodes; Appl Phys Lett; 97(3):1-3; Jul. 2010.

Verma et al.; Surface-structure-regulated cell-membrane penetration by monolayer-protected nanoparticles; Nat Mater; 7(7):588-595; Jul. 2008 (Author Manuscript; pp. 15).

Walker et al.; Effects of flow and diffusion on chemotaxis studies in a microfabricated gradient generator; Lab Chip; 5(6):611-618; Jun. 2005 (Author Manuscript; pp. 18).

Wang et al.; Neural stimulation with a carbon nanotube microelectrode array; Nano Lett; 6(9):2043-2048; Sep. 2006.

Wang et al.; Shear stress induces endothelial differentiation from a murine embryonic mesenchymal progenitor cell line; Arterioscler Thromb Vasc Biol; 25(9):1817-1823; Sep. 2005.

Whitesides; The origins and the future of microfluidics; Nature; 442 (7101):368-373; Jul. 27, 2006.

Wolfe et al.; U.S. Appl. No. 61/306,778 entitled "Neutral Particle Nanopatterning for Nonplanar Multimodal Neural Probes," filed Feb. 22, 2010.

Wu et al.; Generation of complex, static solution gradients in microfluidic channels; J Am Chem Soc; 128(13):4194-4195; Apr. 5, 2006.

Xiao et al.; Fabrication of Alumina Nanotubes and Nanowires by Etching Porous Alumina Membranes; Nano Lett; 2(11):1293-1297; Oct. 26, 2002.

Xie et al.; Vertical nanopillars for highly localized fluorescence imaging; Proc Natl Acad Sci U S A.; 108(10):3894-9; Mar. 2011.

Yang et al.; Semiconductor nanowire: What's Next?; Nano Letters; 10; pp. 1529-1536; May 2010.

Yu et al.; Diffusion dependent cell behavior in microenvironments; Lab Chip; 5(10):1089-1095; Oct. 2005.

Yu et al.; Nano Wheat Fields Prepared by Plasma-Etching Gold Nanowire-Containing Membranes; Nano Lett; 3(6);815-818; Mar. 20, 2003.

Zeck et al.; Noninvasive neuroelectronic interfacing with synaptically connected snail neurons immobilized on a semiconductor chip; Proc Natl Acad Sci U S A.; 98(18):10457-62; Aug. 2001.

Zicha et al.; A new direct-viewing chemotaxis chamber; J Cell Sci; 99 (4);769-775; Aug. 1991.

Zigmond; Orientation chamber in chemotaxis; Methods Enzymol; 162:65-72; Oct. 12, 1988.

Das et al.; TiO2 nanotubes on TI: influence of nanoscale morphology on bone cell-materials interaction; Journal of Biomedical Materials Research Part A; 90(1); pp. 225-237; Jun. 1, 1990.

Oates et al.; Role of titanium surface topography and surface wettability on focal adhesion kinase mediated signaling in fibroblasts; Materials; 4(5); pp. 893-907; May 9, 2011.

Cell Stress

X | 2 hours | 3 days | 5 days
---|---|---|---
SELS | | |
PTX3 | | |
MX1 | | |
SOD1 | | |
TP53TG1 | | |
PTGS2 | | |
SOD2 | | |
MAP4K1 | | |
CYP7B1 | | |
ALOX12 | | |
CYP2E1 | | |
HSP90AA1 | | |
CRP | | |
ALOX5 | | |

Endocytosis

Y | 2 hours | 3 days | 5 days
---|---|---|---
CLTA | | |
CLTB | | |
AP1B1 | | |

Ion Channels

Z | 2 hours | 3 days | 5 days
---|---|---|---
BDKRB1 | | |
SLC11A2 | | |
SCNN1A | | |
KCNN2 | | |

2 fold decrease — no change — 2 fold increase

NANOTUBE STRUCTURES, METHODS OF MAKING NANOTUBE STRUCTURES, AND METHODS OF ACCESSING INTRACELLULAR SPACE

CROSS REFERENCE TO RELATED APPLICATIONS

This application is a continuation of U.S. patent application Ser. No. 13/455,245, filed on Apr. 25, 2012, titled "NANOTUBE STRUCTURES, METHODS OF MAKING NANOTUBE STRUCTURES, AND METHODS OF ACCESSING INTRACELLULAR SPACE", now U.S. Pat. No. 9,266,725, which claims priority to U.S. Provisional Patent Application No. 61/479,423, filed on Apr. 27, 2011, titled "NANOTUBE STRUCTURES, METHODS OF MAKING NANOTUBE STRUCTURES, AND METHODS OF ACCESSING INTRACELLULAR SPACE," and U.S. Provisional Patent Application No. 61/584,421, filed on Jan. 9, 2012, titled "NANOTUBE STRUCTURES, METHODS OF MAKING NANOTUBE STRUCTURES, AND METHODS OF ACCESSING INTRACELLULAR SPACE," each of which are entirely incorporated herein by reference.

FEDERAL SPONSORSHIP

This invention was made with Government support under Contract DE-AC02-76-SF00515, awarded by the Department of Energy, Office of Basic Energy Science. The Government has certain rights in this invention.

BACKGROUND

Delivery of small molecules, proteins, and genetic material across the cell membrane barrier and into the cytosol is a critical step for molecular biology and cell reprogramming techniques, yet efficient, non-disruptive delivery is still often a rate-limiting step.

Methods for cytosolic delivery of biomolecules are essential for a broad range of modern biological techniques, including siRNA knockouts, cell reprogramming, intracellular imaging and pharmaceutical therapeutics. Biological mechanisms are often harnessed to transfer reagents across the cell membrane barrier. Many of these methods are hampered by lysosomal degradation, cell-type specificity, low efficiency, expense, and/or toxicity concern. This has led to more physical approaches to directly breach the cell membrane, such as electroporation or micropipetting, yet these suffer from their own drawbacks. Despite significant advances in bio-active reagent development for biological procedures, effective cytosolic delivery to a significant number of cells is still often a prohibitive step. Thus there is a need to overcome these and other difficulties encountered in delivery of material across the cell membrane barrier.

SUMMARY

In accordance with the purpose(s) of the present disclosure, as embodied and broadly described herein, embodiments of the present disclosure, in one aspect, relate to methods of making a structure including nanotubes, a structure including nanotubes, methods of delivering a fluid to a cell, methods of removing a fluid to a cell, methods of accessing intracellular space, and the like.

One embodiment, among others, of the present disclosure includes a method of making a structure that includes providing a porous structure, wherein at least a portion of the pores extend through the porous structure; disposing a layer of material onto the porous structure, wherein the material forms a layer on the pore walls to form a nanotube having a layer of material as the walls of the nanotube, wherein the porous structure is made of a material that is different than the material of the layer; and removing a portion of the porous structure to expose a portion of the nanotube so that the nanotube extends a distance above the porous structure.

One embodiment, among others, of the present disclosure includes a structure that includes a porous structure having a plurality of nanotubes extending through the porous structure, wherein the nanotubes extend a distance above the porous structure.

One embodiment, among others, of the present disclosure includes a method of delivering a fluid to a cell that includes culturing cells on a structure, wherein the nanotubes have intracellular access to the cells disposed on the nanotubes, wherein the structure is a porous structure having a plurality of nanotubes extending through the porous structure, wherein the nanotubes extend a distance above the porous structure; and flowing a fluid through the nanotubes into the intracellular space of the cells.

One embodiment, among others, of the present disclosure includes a method of removing a fluid to a cell that includes culturing cells on a structure, wherein the nanotubes have intracellular access to the cells disposed on the nanotubes, wherein the structure is a porous structure having a plurality of nanotubes extending through the porous structure, wherein the nanotubes extend a distance above the porous structure; and flowing a fluid through the nanotubes out of the intracellular space of the cells.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 2A is a schematic of cell cultured on nanostraw membrane with microfluidic channel access. FIGS. 2B to 2E illustrates a nanostraw fabrication process flow that begins with a nanoporous polycarbonate membrane (FIG. 2B), proceeds with a conformal alumina atomic layer deposition (FIG. 2C), then an alumina specific directional reactive ion etch (FIG. 2D), and concludes with a polycarbonate specific directional reactive ion etch (FIG. 2E). FIGS. 2F and 2G illustrate scanning electron micrographs of nanostraw membranes.

FIG. 2H illustrates an embodiment of a microfluidic device used to deliver biomolecules into cells via nanostraw-mediated delivery. FIGS. 2I and 2J illustrate SEM images of critical point dried (CPD) cells cultured on nanostraw membranes with 100 nm diameter straws at a density of $10^8$ straws/cm$^2$.

FIG. 2R is a depiction of the localization of dyes internalized via endocytosis (red), in contrast to diffuse nanostraw-mediated delivery (green). FIG. 2S illustrates confocal microscopy that shows that all cells exhibit vesicular fluorescence while a subset of cells exhibit cytosolic fluorescence. When uptake methods are observed independently, cells still exhibit cytosolic fluorescence (FIG. 2T) after nanostraw mediated delivery, and vesicular fluorescence (FIG. 2U) when cultured in dye-supplemented media. Z-slices of a characteristic cell show that this difference in dye distribution is observed throughout the entire cell body for nanostraw-mediated delivery (FIG. 2V, dashed box in FIG. 2T), and for endocytosis from dye-supplemented media (FIG. 2W, dashed box in FIG. 2U).

FIGS. 2X to 2Z illustrate cells cultured on membranes with and without nanostraws shows minimal change in gene expression. Heat maps for genes associated with (FIG. 2X) Cell stress, (FIG. 2Y) Endocytosis, and (FIG. 2Z) Ion channels, demonstrates negligible changes in expression.

FIG. 3A also illustrates an SEM micrograph of a CHO cell cultured on nanostraws.

FIG. 4A illustrates a side view and expanded inset of cells cultured on top of the nanostraw membrane. FIG. 4B illustrates an optical image of an actual device with a 250 µm wide fluidic channel underneath the nanostraw membrane. Green dye added to visualize the channel.

FIGS. 4C and 4D illustrate SEM images of 100 nm diameter, 500 nm tall nanostraws with 30 nm pores. These nanostraws each connect to a microfluidic channel beneath the supporting membrane. FIGS. 4E and 4F illustrate CHO cells incubated on the nanostraws show excellent spreading and morphology. FIG. 4G illustrates live/dead assay of CHO cells on the nanostraw platform after 3 days shows excellent cell viability even when pierced. FIG. 4H illustrates direct access/cell penetration was verified by delivering GFP plasmid into the fluidic channel, resulting in GFP expression by the cultured cells. Cells away from the channel were not affected.

FIG. 4I illustrates a diagram of fluidic resistance. FIG. 4J illustrates a molecule current for different radii nanostraws. For a 30 nm radius pore through a 10 µm long straw, approximately 100 molecules will diffuse through per hour for cellular abundances of $\sim 10^4$ molecules/cell.

FIG. 5B illustrates a lateral gradient in the flow channel is diffusively delivered to the cell culture area.

FIG. 5F illustrates that fluorescent intensity is normalized to the peak intensity, and dashed lines indicate the channel edges. The solid line represents an FEM simulation of the signal concentration 3 μm above the top membrane surface after 20 minutes. For illustrative purposes, the membrane in the simulation has 10% porosity. The line simulates the signal presented to the cell surface. After diffusing through the membrane, the source signal is reduced in peak intensity and signal fidelity, and extends beyond the original channel.

DETAILED DESCRIPTION

Figure 1A:
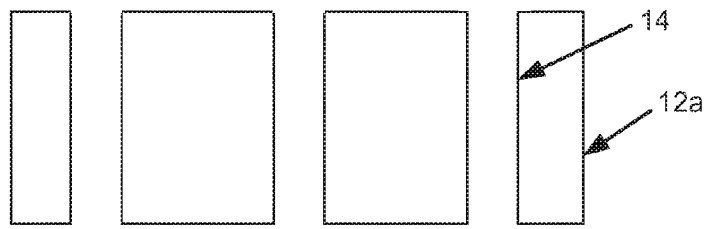
FIGS. 1A to 1D and 1E to 1H (perspective view of FIGS. 1A to 1D) illustrate an exemplary method of making a structure of the present disclosure.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of fluidics, fabrication, chemistry, biology, and the like, which are within the skill of the art. Such techniques are explained fully in the literature.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Discussion

In accordance with the purpose(s) of the present disclosure, as embodied and broadly described herein, embodiments of the present disclosure, in one aspect, relate to methods of making a structure including nanotubes, a structure including nanotubes, methods of delivering a fluid to a cell, methods of removing a fluid to a cell, methods of accessing intracellular space, and the like.

In particular, embodiments of the present disclosure include structures including a porous structure, methods of making a porous structure, methods of using a porous structure, methods of intracellularly introducing a fluid/species into a cell and/or removing fluid/species from a cell, and the like. As described in more detail herein, the porous structure includes a plurality of nanotubes extending through the porous structure so that fluid and/or species can flow and/or diffuse through the nanotubes. In an embodiment the species can be chemical or biological species.

In an exemplary embodiment, the porous structure can be used as an intracellular delivery platform and/or a cell sampling platform. In an exemplary embodiment, one or a combination of the materials can be flowed (e.g., delivered) using the nanotubes: salts and molecular ions in solution, small molecules, proteins, genetic material (e.g., DNA, RNA, siRNA, and miRNA), synthetic constructs and nanoparticles, combinations of any of these, and the like. In an exemplary embodiment, one or more of the materials described herein can be selectively delivered to cells penetrated by the nanostraws, selectively delivered to cells positioned over fluidic channels containing specific cargo, and/or directed delivery of release agents to only selected cells for extraction, for example.

In an exemplary embodiment, the porous structure can be used in cell differentiating, cell reprogramming, gene therapy, cell maintenance, altering protein expression, labeling cells and cell components, influencing signaling pathways, altering cell behavior, cell treatment, delivery of tissue samples (e.g., brain slices, multiple dermal layers, etc.), gene transfection, stem cell differentiation, drug delivery, and other fundamental biochemistry and biophysics research.

In an exemplary embodiment, the porous structure can be used for extraction of cellular material for facilitation of cell-cell communication, non-destructive sampling of cellular components both internal and external to cells, and the like.

In an exemplary embodiment, the porous structure can be used to sense or detect material such as salts, ions, small molecules, proteins, genetic material, synthetic constructs, nanoparticles, and the like, as well as specific molecules found in cellular environments both internal and external to cells.

In an exemplary embodiment, the porous structure can be used for forming stable interfaces for electrical measurements of cell behavior.

In an exemplary embodiment, the porous structure can be used in sorting applications for cells by functionalization to interact with specific cells and differentiate two or more populations of cells, selected intracellular delivery to those cells, and selected release of cells.

Furthermore, the porous structure can be used for intracellular assays and live in vitro cell sampling and monitoring. In another embodiment, the porous structure can be used for transdermal drug delivery. In another embodiment, the porous structure can be used to focus and concentrate electroporation fields.

Other transmembrane devices are serial and manual (such as cellular microinjection and traditional patch-clamping) or cannot use fluidic sources, limiting the delivery target variety, and requiring pre-loading of a single dose agent.

An embodiment of the present disclosure can be used as a surface to culture cells (e.g., single cells to $10^7$ cells or more). The cells grow, adhere, and proliferate on the nanotubes spontaneously and provide a reliable long-term intracellular access to a cell(s) without affecting their healthy functioning and can live for days or a week or more. Furthermore, combining the porous structure with a fluidic device allows for automation, which can increase throughput and efficiency while reducing reagent costs. Additional details are provided herein and in the Examples.

Figure 1B:
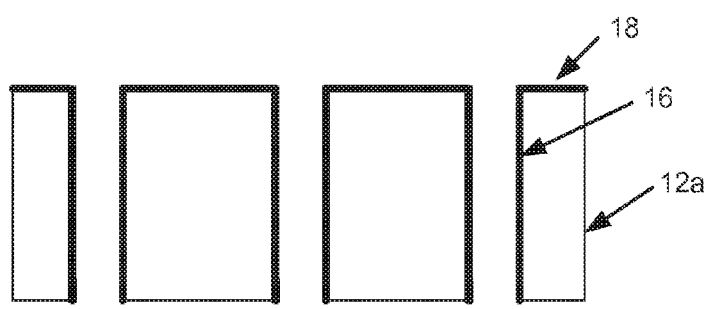
Figure 1C:
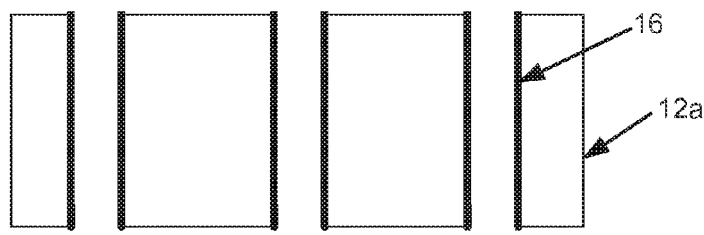
Figure 1D:
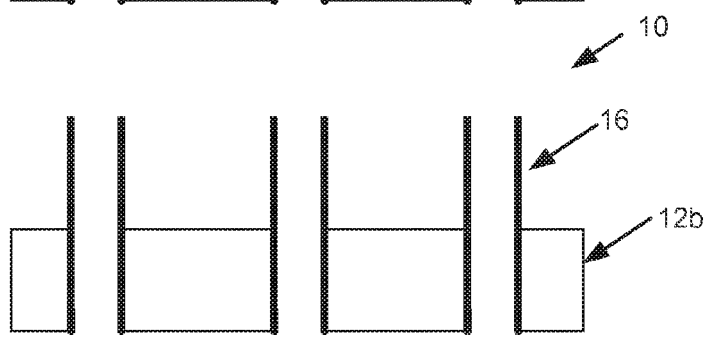
Figure 1E:
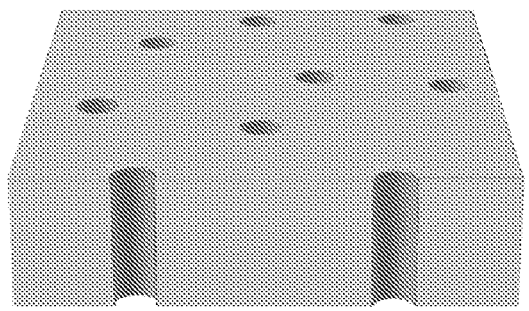
Figure 1F:
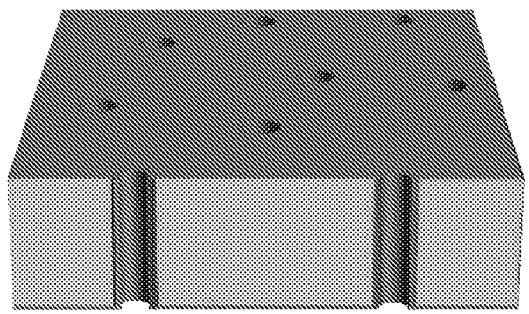
Figure 1G:
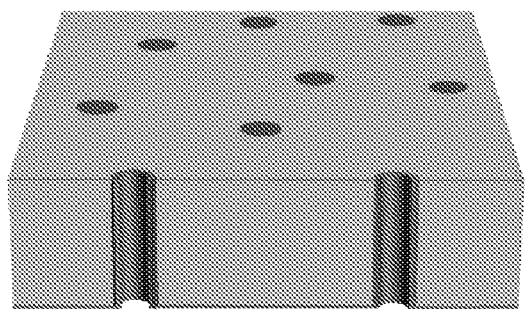
Figure 1H:
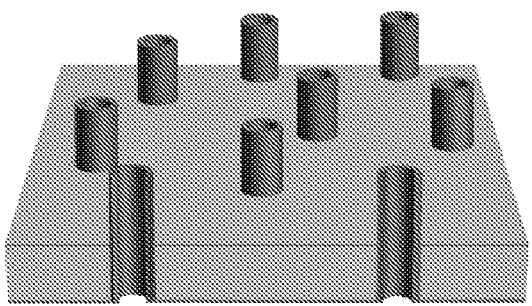

An embodiment of the present disclosure includes a structure having a porous structure, where the porous structure includes a plurality of nanotubes extending through the porous structure (See FIG. 1D). The nanotubes extend a distance above the porous structure and extend through the porous structure. The term "nanotube" is also referred to as a hollow nanowire or a nanostraw.

A material, such as a fluid, can flow through the nanotubes, or species in the fluid can diffuse through the tubes. A portion or all of the nanotubes can be in fluidic communication with a device or area on either side of the porous structure so that a material can pass through the nanotubes in either direction. For example, a fluid can flow from the bottom of the porous structure (the side opposite the nanotubes extending above the porous structure) out of the nanotubes extending from the surface of the porous structure. In another example, a fluid or species can move from the top portion of the structure (the side where the nanotubes extend above the porous structure and into cells in a cell culture, for example) through the nanotube and out of the bottom portion of the structure, where, for example, the species can be removed, analyzed, modified, filtered, detected, any combination of these, and the like.

In an embodiment, the fluid (e.g., including materials as described herein) can be flowed through the one or more nanotubes using one or more of the following: control of pressure, applying electric and/or magnetic fields, controlling osmotic and/or concentration gradients, use of surface interactions and/or species-species interactions, physical inducement such as centrifugal, flow, and/or shear effects.

In an embodiment, the structure can be interfaced with a fluidic device. In an embodiment, the fluidic device can be positioned to be in fluidic communication with the bottom of the porous structure so that fluid can flow through the nanotubes. The fluid can flow from the fluidic device through the nanotubes and/or fluid can flow from the nanotubes into the fluidic device.

In an embodiment, the porous structure is the bottom surface of a holding structure (e.g., cell culture dish). In an embodiment, the holding structure includes walls that form the side boundary of the holding structure. The nanotubes extending above the porous structure surface extend up into the area bounded by the walls and the porous structure. In an embodiment, a material can be disposed in the holding area. In a specific embodiment, cells can be cultured in the holding area and the nanotubes can be in fluidic communication with the intracellular fluid of the cell. In an embodiment, a fluidic device is in communication with the nanotubes so that fluid and/or species can be introduced into and/or removed from the holding areas (e.g., into and/or out of the cell). Additional details are described in the Examples.

As mentioned above, the porous structure includes a plurality of pores that extend through the porous structure so that a material can pass from one side of the porous structure to the other side of the porous structure. Said differently, the pores are like channels that extend through the porous structure. In an embodiment, the porous structure can include pores of the same diameter or of different diameters. In an embodiment, the pores can be randomly positioned (e.g., using a porous membrane) or can be aligned in a specific pattern (e.g., an addressable array). In an embodiment, the porous structure, after etching, (See discussion associated with FIGS. 1A to 1D) can have a thickness of about 100 nm to 50 μm or about 15 to 25 μm. In an embodiment, the porous structure, prior to etching, can have a thickness of about 1 to 50 μm or about 10 to 30 μm. In an embodiment, the porous structure can have an area of about 1 mm$^2$ to 500 cm$^2$ or about 1 to 80 cm$^2$.

In an embodiment, the porous structure can be made of a material that can be etched. In an embodiment, the porous structure can be made of a material such as polycarbonate, polyester, and/or a polymer, that can be processed with pores, silicon, or a combination thereof. In a particular, embodiment, the polymer can include polyethylene terephthalate (PET), polylactic acid (PLA), polyglycolic acid (PGA), PLGA, layer-by-layer polyethylene imine/polyacrylic acid, NiPAAM, protein hydrogels, and a combination thereof. In a particular, embodiment, the material can include protein mixtures (e.g., Matrigel®), tissue-based substrates, feeder cell layers, and the like, and a combination thereof.

In an embodiment, the porous structure can include a layer (a bottom layer) of material disposed on the side opposite the nanotubes extending from the surface. In an embodiment, the layer is made of a material that is the same as the nanotubes (see below) or of a different material. In an embodiment, the porous structure can include a layer of material disposed on the same side as the nanotubes extending from the surface, where the thickness of the top layer is not larger than the length of the nanotube extending above the porous structure. In an embodiment, the layer (a top layer) is made of a material that is the same as the nanotubes (see below) or of a different material.

In an embodiment the nanotubes can extend above the surface of the porous structure about 2 nm, to 50 µM, about 100 nm to 20 µm, or about 1 to 5 µm. In an embodiment the nanotubes can have a total length (in the porous structure and extending from the porous structure) of about 1 to 50 µm or about 10 to 25 µm. In an embodiment all of the nanotubes can extend above the surface of the porous structure the same distance. In another embodiment a portion of the nanotubes can extend a first distance and another portion of the nanotubes can extend a second distance, where the first and second distances are different. In another embodiment a plurality of groups of nanotubes can each have different lengths above the porous structure.

In an embodiment all of the nanotubes can have the same inner diameter. In another embodiment a portion can have a first diameter and another portion can have a second diameter, where the first and second diameters are different. In another embodiment a plurality of groups of nanotubes can each have different diameters. In an embodiment, the nanotubes can have an inner diameter of about 5 nm to 700 µm or about 20 to 80 nm. In an embodiment, the nanotubes can have a wall thickness (or outer diameter) of about 5 to 500 nm or about 10 to 30 nm.

In an embodiment, the nanotube can be made of a mechanically stable material that may also have one or more of the following properties: optical transparency, conductance, surface charge state, or chemical reactivity. In an embodiment, the nanotube can be made of a material such as alumina ($Al_2O_3$), $TiO_2$, $SnO_2$, $ZrO_2$, $ZnO_2$, carbon, nitrides, platinum, gold, silver, indium tin oxide (ITO), $SiO_2$, Ni, NiO or related transition metals and their corresponding oxides and nitrides, or a combination thereof. In an embodiment all of the nanotubes can be made of the same material. In another embodiment, a portion of the nanotubes can be made of a first material and a second portion can be made of a second material, where the first a second material are not the same.

In an embodiment, the number of nanotubes can be 1 to hundreds, to thousands, to millions, to 10s of millions, to 100s of millions, or more, which can depend, in part, upon the area of the porous structure and the desired use of the structure.

It should be noted that the dimensions of the porous structure and the nanotubes, as well as the number of nanotubes and the materials of each of the porous structure and the nanotubes can be designed for each specific use. The descriptions provided herein are exemplary.

In an exemplary embodiment, a portion (e.g., tip (e.g., outside, inside, bottom, and/or top); a portion or all of the, inside of the nanotube, outside of the nanotube, or base of the nanotube; and combinations thereof) of a nanotube can be coated with one or more types of materials on one or more surfaces of the nanotubes. In an embodiment, different tubes can be coated with different materials or some nanotubes can be coated and other nanotubes remain uncoated. In an embodiment, a portion of the nanotube can be coated with a metal film, which can be used to facilitate electrical interfaces and/or electrokinetic manipulation. In an embodiment, a portion of the nanotube can be coated with a ceramic coating, which can provide structural integrity and/or alter surface energy characteristics. In an embodiment, a portion of the nanotube can be coated with a synthetic coating, which can alter surfaces and/or enhance functionality such as adhesion or repulsion. In an embodiment, a portion of the nanotube can be coated with a catalytic coating. In an embodiment, a portion of the nanotube can be coated to control surface behavior and/or properties including opacity and hydrophilicity. In an embodiment, a portion of the nanotube can be coated to control modulation of external probes including physical probes, electric fields and currents, electromagnetic radiation, and the like for optical or spectroscopic observation.

In particular, the tip of the nanotube can be coated with a coating that interacts with and/or detects intracellular concentrations of materials in the cell or products of cellular processes. In an embodiment, the tip of the nanotube can be coated with indicators, sensors, and/or capture agents to monitor and/or influence intracellular behavior. In an embodiment, the tip of the nanotube can be coated with synthetic constructs to such plasmonic nanoparticles and other nanostructures, synthetic biomolecules, and/or bio-organic hybrid materials. In an embodiment, the tip of the nanotube can be coated with agents to determine the extent of interactions between nanotubes and specific targets such as specific types of cells in a population.

In particular, the sides or portions of the sides of the nanotube can be coated with metal or ceramic coatings or bands. In particular, the sides or portions of the sides of the nanotube can be coated with surface functionalization coatings with specific molecules.

In particular, the base or portions of the base of the nanotube can be coated with materials to influence adhesion, promote penetration, and/or prevent interactions. In addition, the base or portions of the base of the nanotube can be coated with materials that can serve as templates or molds for the fabrication of other structures or features. In an embodiment, the base or portions of the base of the nanotube can be coated with materials to enhance functionality of standard uses for track-etched membranes such as filtration due to specific surface properties, coatings, and/or nanotube features.

In an embodiment, different fluids can be selectively flowed through different sets of nanotubes in an addressable manner. In this way the same types of cells can be studied and analyzed using different materials.

The structure can be made using one or more methods. FIGS. 1A to 1D and 1E to 1H (perspective view of FIGS. 1A to 1D) illustrate an exemplary method of making a structure of the present disclosure. Although not described in reference to FIGS. 1A to 1D and 1E to 1H, coatings, such as those mentioned above, can be disposed on portions of one or more nanotubes. Additional methods of making embodiments of the present disclosure are described in the Examples.

Now referring to the figures, FIG. 1A illustrates a porous structure including the porous structure material 12a and pores 14. The characteristics of the pores 14 and the porous structure material 12a and the materials of the porous structure material 12a are described herein. In an embodiment, the porous structure is a porous membrane that can be commercially purchased.

FIG. 1B illustrates the porous structure having a layer of material 18 disposed on the top of the porous structure and on the walls of the pores 14 to form a nanotube 16. The material to form the nanotube 16 and the characteristics of the nanotube are described herein. In an embodiment, the layer of material can be disposed on the porous structure (See Examples). The layer of material 18 can be disposed using techniques such as, for example, atomic layer deposition, electroless deposition, electro deposition (for conducting substrates), sputtering, chemical vapor deposition (CVD), and plasma based deposition systems.

FIG. 1C illustrates the porous structure having the layer of material 18 removed from the top of the porous structure but not the walls of the pores 14. By removing the layer of material 18 on top, the porous structure material 12a is exposed and can be etched. The layer of material 18 can be removed using techniques such as, for example, reactive ion etching, planar etching, chemical-mechanical planarization, mechanical polishing, wet chemical etching, and dry plasma etching.

FIG. 1D illustrates the structure 10 where the nanotubes 16 extend above the surface of the porous structure. The nanotubes 16 are exposed by removing a portion of the porous structure material 12a so that only specified thickness of porous structure material 12b remains. The amount of porous structure material 12a removed can be controlled by the etching process. The amount of porous structure material 12a removed controls the distance that the nanotubes extend above the surface of the porous structure. The porous structure material 12a can be removed using techniques such as, for example, reactive ion etching, planar etching, wet chemical etching, and dry plasma etching In an embodiment, the etchant should be selective for material 12a, and etches material 16, and does not mechanically disturb the surface (as in mechanical polishing). In this regard, material 12 is individually etchable, and material 16 is able to be deposited conformally, and be mechanically robust enough to support its own straw structures.

In an embodiment, electrically active materials could be deposited onto the underside of the polymer membrane (the opposite side to the nanostraws) to provide electrical pickup and deliver electrical current. These materials include both Faradaically active materials, such as carbon, Ir, Pt, Au, or Ag, or capacitively active materials, such as $Ir_2O_3$, PtO, permanganate, or other high capacitance materials known in the art. These materials could extend some portion into the nanopores, or could bridge over them, or could be located around the pore without occlusion.

EXAMPLES

Now having described the embodiments of the present disclosure, in general, the following examples describe some additional embodiments of the present disclosure. While embodiments of the present disclosure are described in connection with the examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Delivery of small molecules, proteins, and genetic material across the cell membrane barrier and into the cytosol is a critical step for molecular biology and cell reprogramming techniques, yet efficient, non-disruptive delivery is still often a rate-limiting step. Here we demonstrate cell-culture platforms of fluidic "nanostraws" pierce the cell membrane, providing a permanent pipeline to the inside of the cell for direct material delivery. Conventional polymeric track-etch cell culture membranes are alumina coated and etched to produce fields of nanostraws with controllable diameter, thickness and height. Each nanostraw is fluidically connected to the bottom of the polymer membrane, allowing chemicals located under the cell culture area to diffuse through the nanostraws and directly into the cells. Ions, small molecules, and green-fluorescent-protein-encoding DNA plasmids were successfully transported into the cytosol with efficiencies up to 70%. Depending on the underlying fluidic chamber design, species could be delivered uniformly over large areas of ~$10^6$ cells, or selectively within a narrow band. Although not all nanostraws penetrated the cell membrane, those that did remained open over extended periods, enabling sequential chemical delivery and modulation. Remarkably, nanostraw penetration does not appear to perturb the cells, as both live/dead assays and mRNA gene chip analysis show no statistical differences with control populations. These platforms open the way for simple, reproducible delivery of a wide variety of species into cells without endocytosis.

Methods for cytosolic delivery of biomolecules are essential for a broad range of modern biological techniques, including siRNA knockouts, cell reprogramming, intracellular imaging and pharmaceutical therapeutics {79 Tiscornia, G. 2003; 80 Plath, Kathrin 2011; 10 Michalet, X. 2005; 24 Carter, Paul J. 2006; 17 Heath, James R. 2008}. Biological mechanisms are often harnessed to transfer reagents across the cell membrane barrier, such as viral vectors for gene delivery {{79 Tiscornia, G. 2003; 76 Hanna, Jacob 2009}} and endocytotic uptake of cargo, using carriers like lipofectamine {{10 Michalet, X. 2005; 24 Carter, Paul J. 2006; 17 Heath, James R. 2008; 81 Choi, Mi-Ran 2007}}. These methods are hampered by lysosomal degradation, cell-type specificity, low efficiency, expense, or toxicity concerns {{55 Adler, Andrew F. 2010}}. This has led to more physical approaches to directly breach the cell membrane, such as electroporation or micropipetting, yet these suffer from their own drawbacks. {{82 Chu, G. 1987; 83 Susin, S A 1999}}. Despite significant advances in bioactive reagent development for biological procedures, effective cytosolic delivery to a significant number of cells is still often a prohibitive step {{59 Luo, Dan 2000}}.

Recently, nanomaterial platforms have been used to improve intracellular delivery. While two-dimensional surface patterning and texturing have long been used to affect cell behavior {{32 Kubota, Y. 1988; 44 Ruoslahti, E. 1987; 61 James, C. D. 1998}}, high-aspect ratio nanowires open an entirely new avenue for cellular interaction due to their potential for direct membrane penetration {{35 Kim, Woong 2007; 50 Yang, Peidong 2010; 51 Tian, Bozhi 2010; 37 Xie, Chong 2011}}. By functionalizing nanowires with bioactive molecules, intracellular delivery has been demonstrated {{34 McKnight, T. E. 2004; 36 Shalek, Alex K. 2010}} while maintaining cell viability and behavior {{38 Qi, Suijian 2009}}. These exciting new methods are very promising, yet are restricted to molecules that can be linked or otherwise bound to the nanowires, and offer little temporal or concentration control. Alternatively, functionalized scanning probes or pipettes can be used to inject selected cells,[1,2] yet these serial processes are cumbersome for large numbers of cells.

Biological systems have also developed blueprints for stable conduits through the cell wall. These include gap junction proteins that facilitate intercellular diffusion of chemical species between eukaryotic cells, {{48 Kumar, N. M. 1996; 57 Alberts, Bruce 2002}} and ~100 nm diameter hollow lipid nanotubes between bacteria, transmitting proteins and conferring antibiotic resistance to neighboring bacteria {{39 Dubey, Gyanendra P. 2011}}. These nanoscale intercellular junctions provide fluidic access and promote molecular exchange, yet are small enough to avoid cell toxicity. Inspired by this design, here we report a simple biomimetic 'nanostraw' platform that establishes continuous fluidic access into the cell interior for the delivery of small molecules, proteins, and genetic material. (FIG. 2A) Cells that are cultured on nanostraws of sufficiently small diameter (~100 nm) are spontaneously penetrated, though the mechanism is not yet fully understood. Biomolecules added to a fluidic chamber beneath the nanostraw membrane diffuse through the nanostraws and into the cell, providing a direct intracellular fluidic conduit with external chemical control.

We use a simple and reproducible nanofabrication method to produce fields of uniform nanostraws with controllable dimensions. A wide array of molecules can be delivered to large culture areas containing ~$10^6$ cells or more. In addition, nanostraw interface stability and microfluidic manipulation enable time-resolved, sequential delivery to cells while maintaining the low perturbation of a nanostructured delivery system. We demonstrate external modulation of internal cellular content over minute timescales, as well as DNA plasmid delivery and transfection using nanostraw delivery. Nanostraw-mediated delivery is effective for up to 70% of cells in culture and occurs by direct cytosolic delivery and not extracellular uptake. The reliability, time resolution, large area delivery, and versatility demonstrated by nanostraw delivery can lead to an effective, functional intracellular delivery platform.

Nanostraw Fabrication

Figures 2A, 2B, 2C, 2D, 2E, 2F, 2G:
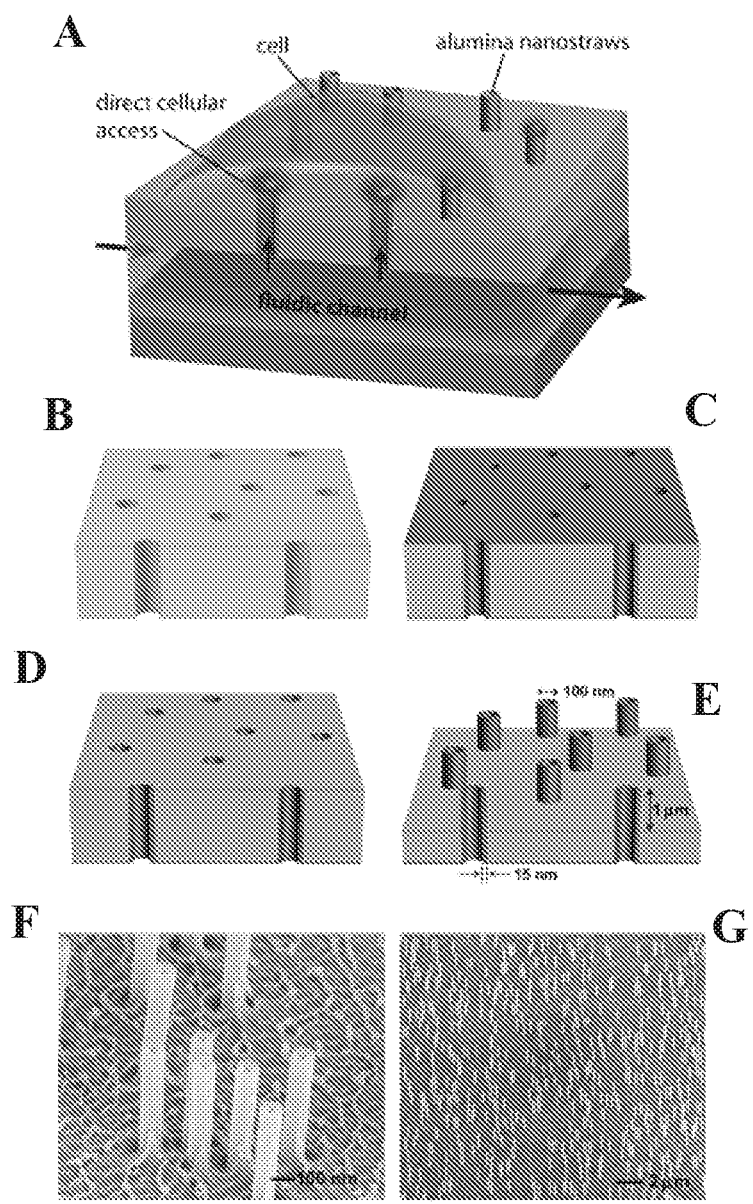
FIGS. 2A to 2G illustrate an embodiment of a nanostraw-cell interfacing strategy and fabrication.

Nanostraws were fabricated starting with track-etched polycarbonate membranes {{53 Martin, Charles R. 1994}}, widely used for cell-culture and water purification {{42 Keenan, Thomas M. 2008; 67 Bernards, Daniel A. 2010}}), as a template. These membranes are commercially available (AR Brown-US, Long Beach, Calif.) in a range of pore sizes (~20 nm-10 µm) and pore densities. In this study devices were fabricated with membrane pore diameters ranging from 100 to 750 nm and pore densities of $10^6$, $10^7$, and $10^8$ pores/cm² (FIG. 2B). First, an alumina coating was deposited on all nanoporous membrane surfaces (top, bottom, and inside the pores) with atomic layer deposition (ALD), yielding a uniform coating typically chosen to be 15-30 nm thick (FIG. 2C). The deposited alumina creates the nanostraw bodies within the nanopore interiors, and defines the nanostraw wall thickness. Next, the alumina on the top surface was removed with a directional reactive ion etch (RIE) to expose the bare polymer layer underneath (FIG. 2D). Finally, an oxygen RIE was used to expose the nanostraws by selectively etching the polymer until the desired nanostraw height was obtained, typically 1-2 µm (FIG. 2E). The oxygen RIE is highly selective for polycarbonate, ensuring that the alumina comprising the nanostraws is not degraded as the straws are created.

The nanostraw dimensions are independently controllable though adjustments to the track-etched membrane properties (straw diameter and density), ALD alumina thickness (straw wall thickness), and etch time (nanostraw height). These microfabrication processing steps can easily create large area, 100 mm petri-dish sizesheets of nanostraws. Scanning electron microscopy (SEM) confirmed that the process yields well-defined nanostraws on the top side of the membranes for all membranes tested (FIGS. 2F and 2G). The nanostraw height, wall thickness, and inner diameter were highly uniform (±10%, within the tolerance of the original pore sizes) across centimeter-scale membranes. Nanostraws with aspect ratios as high as 10:1 were created with essentially quantitative yields. The dimensions of the smallest nanostraws are comparable to those of nanowires previously used for direct delivery {36 Shalek, Alex K. 2010}, while the largest nanostraws resemble structures used for neural interfacing {65 Zeck, Gunther 2001}. The oxygen etch leaves a slightly textured polycarbonate surface (FIG. 2F), however this did not adversely affect cell culture.

The track-etched nanoporous membrane template is advantageous for several reasons. First, it is commonly available and an excellent cell culture substrate. Secondly, nanopores are available in a large range of diameters, while pore sizes within a single membrane are relatively monodisperse and create uniform nanostraws over very large areas. Finally, the 'self-aligned' fabrication process ensures that each nanostraw is fluidically connected to the bottom of the membrane without the need for top-down nanostraw-pore alignment. Further fabrication steps can also introduce different material layers within the nanostraws, or surface-modify the alumina as desired.

Direct Delivery into Cells Using Nanostraws

Figures 2H, 2I, 2J:
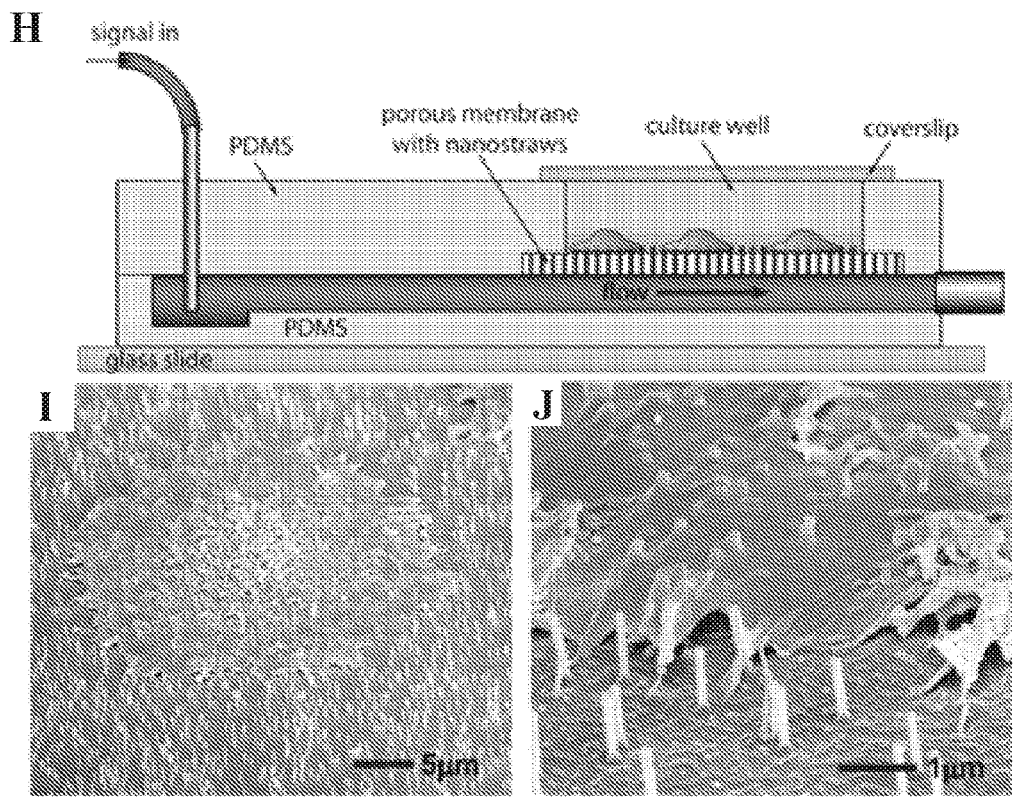
FIGS. 2H to 2J illustrate an embodiment of a device schematic overview.

Reagent delivery through the nanostraws and into penetrated cells is regulated by controlling the solution composition underneath the polymer/nanostraw membrane. This could be as simple as suspending the membrane over a small dish with the desired solution, or integrating the membrane on top of a microfluidic channel for rapid solution exchange or spatial concentration gradients. In this study the nanostraw membrane is placed on top of two different fluidic devices depending on the number of cells required. For spatially selective delivery the membrane is suspended over a microfluidic channel 0.25-1 mm wide, ~100 µm deep and ~1 cm long, as shown in FIG. 2H. For large cell cultures the nanostraw membrane is supported over a single fluidic chamber approximately 1 cm×1 cm×0.1 cm in size with an external access tube. A second PDMS layer with a cut-out area defining the cell culture region (sized slightly smaller than the nanostraw membrane) is then bonded on top. Solutions introduced into the fluidic channel beneath the membrane diffusively travel through the nanostraws, either into a cell or the cell culture area. A similar platform for extracellular chemical delivery without the nanostraws was recently reported, and found molecular delivery rates agreed with analytical diffusion models. {{88 VanDersarl, Jules J. 2011}} Simple one-dimensional diffusion calculations estimate small molecules such as ions (D~100 m²/s) should diffuse through the 10 µm-thick polymer membrane and straws in ~50 s, while larger proteins (D~10 µm²/s) may take up to 10 min.

After microfluidic integration, the device is flushed with bovine serum albumin (BSA) to minimize reagent adhesion to the walls, and cells are plated onto the nanostraws. Note that cells may simply be added on top of the nanostraw membrane, avoiding complications of injection or encapsulation in microfluidic chambers. Both HeLa or CHO cells cultured in 10% serum spread normally on the nanostraws compared with control samples without nanostraws, even proliferating and dividing at longer timescales (FIGS. 2I and 2J). Cells grew equally well on nanostraw membranes supported on PDMS and suspended over the microfluidic channel.

Figures 2K, 2L, 2M, 2N, 2O, 2P, 2Q:
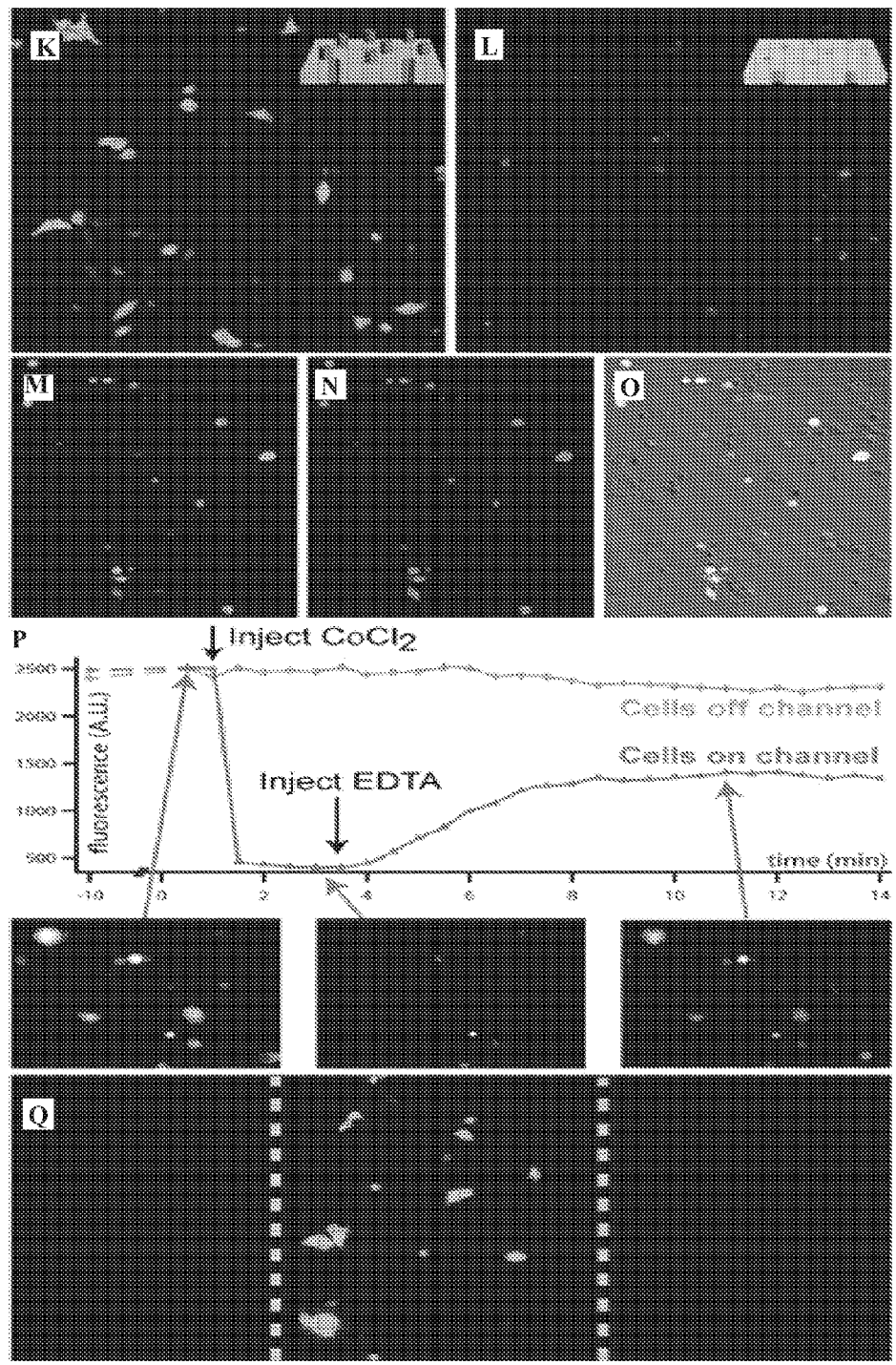
FIGS. 2K to 2O illustrate an embodiment of molecular delivery techniques using nanostraws. Epifluorescence micrographs of replated cells after 24 hour delivery of Alexa-Fluor 488-hydrazide membrane impermeant dye (FIG. 2K) with a nanostraw membrane and (FIG. 2L) with a nanostraw-free membrane. After dye delivery through nanostraws, the cells demonstrate various levels of cell penetration and cytosolic fluorescence. Epifluorescence micrographs of (FIG. 2M) Alexa-Fluor 488-hydrazide dye delivered for 24 hours, (FIG. 2N) Alexa-Fluor 568-hydrazide dye sequentially delivered 12 hours after Alexa-Fluor 488-hydrazide dye, and (FIG. 2O) a composite image demonstrating colocalization of dyes confirms long-term stability of nanostraw access.
FIG. 2P illustrates a GFP-CHO fluorescence quenching using $CoCl_2$ and subsequent fluorescence recovery using EDTA demonstrates short term delivery timescales and the ability to modulate and observe cell behavior in situ.
FIG. 2Q illustrates a nanostraw-mediated GFP transfection of CHO cells cultured over a microfluidic channel (defined by dashed lines) imaged 72 hours after plasmid delivery shows functional molecule delivery.

We demonstrate direct fluidic delivery through the nanostraws by introducing membrane-impermeable fluorescent dyes, ions, and green fluorescent protein (GFP) plasmid into the cell cytosol, which would normally be blocked by the cell membrane. These molecules, along with RNA, large proteins, and many other biomolecular tools used in cell studies, are generally unable to enter the cytosol without a transport agent {{87 Langer, R. 1998}}. FIG. 2K shows cells dyed with Alexa-Fluor 488 Hydrazide, a membrane-impermeant dye. Cells were allowed to adhere for one hour on a large-area cell culture device, then the dye introduced into the underlying fluidic chamber for a fixed period, between 2-24 hrs. At the end of the delivery period, cells were trypsonized, replated and imaged, as in-situ imaging was hampered by the background fluorescence of dye adsorbed to device walls. Cells cultured on large (250 and 750 nm) diameter straws were exposed to higher dye concentrations than cells cultured on 100 nm diameter nanostraws due to higher molecular flux through the nanostraws. However, cells cultured on these large straws did not show dye uptake, while straws on 100 nm straws showed significant fluorescence (FIG. 2K). This fluorescence increase indicates that 100 nm diameter straws penetrate the cell membranes, while larger straws do not. This result agrees with previously reported work, where ~100 nm diameter nanowires were used to successfully deliver biomolecules into cells {{36 Shalek, Alex K. 2010}}. Control experiments on polymer membranes without nanostraws were marked by very weak fluorescent staining, consistent with low-level endocytotic uptake (FIG. 2L). Nanostraw-mediated delivery was also not limited to one cell type, as both HeLa and CHO cells were successfully dyed.

Since cell membranes are highly dynamic and can self-heal transient membrane pores, whether the nanostraw-cytosol connection remains open after the initial penetration event is an important question. A stable fluidic interface is highly preferable for temporal control of chemical delivery, and could even enable extraction and external detection of cytosolic proteins. We tested the stability of the nanostraw fluidic interface by delivering two different membrane-impermeant dyes at proscribed time intervals (FIGS. 2M-2O). In this experiment, if cells which accept the first dye (Alexa-Fluor 488-hydrazide, green) do not accept the second (Alexa-Fluor 568-hydrazide, red), then the interface sealed over the time period between deliveries and is therefore not stable. We tested the interface by delivering the second dye either 2 or 12 hours after the first. As shown in FIGS. 2M-2O, the dyes co-localized in >99% of cells for both time points, demonstrating that the fluidic interface remains open and stable over extended periods. Interestingly, the stained cells displayed several different fluorescence intensities, suggesting that the number of penetrating straws per cell may vary. The cell intensities generally followed an exponential or Poisson distribution, implying that cell membrane penetration is a stochastic process which we estimate to be roughly 1-10% efficient per nanostraw. However, as there are tens to hundreds of nanostraws underneath a typical 10 μm×10 μm adherent cell at straw densities of $10^7$-$10^8$, overall delivery success per cell can be over 70%.

Spatially and Temporally Controlled Delivery

A high degree of spatial and temporal control over chemical delivery is possible by using microfluidic technology to control the solution composition beneath the nanostraws. Time resolved delivery is valuable as it allows for more flexibility in experimental design, greater control over the cellular environment, and finer resolution for investigating cellular response to a signal. Temporal control of nanostraw mediated delivery was investigated through fluorescence quenching and recovery observed in situ. Constitutively GFP-expressing CHO cells were plated in serum onto nanostraws to establish fluidic access, and then exposed to pulses of $CoCl_2$ and ethylene-diamine-tetra-acetic acid (EDTA) to quench and de-quench GFP fluorescence. $Co^{e+}$ quenches fluorescence {{77 Petronilli, V. 1999}}, but must be delivered directly to the cytosol due to low trans-membrane permeability. Subsequent introduction of EDTA into the cells complexes free $Co^{2+}$ and results in partial fluorescence recovery. Fluorescence imaging before, during, and after quenching demonstrated that only cells positioned over the microfluidic channel were affected. This spatial selectivity confirms that extracellular $CoCl_2$ in the cell culture solution (present due to diffusion through nanostraws not penetrating cells) was insufficient for fluorescence quenching and that direct nanostraw delivery of $Co^{2+}$ into cells was responsible. These cells were marked by significant reductions in fluorescence within one minute of $Co^{2+}$ introduction in the microfluidic channel (FIG. 2P). Subsequent delivery of EDTA allowed 75% of quenched cells to regain fluorescence over roughly four minutes. This fluorescence "blinking" demonstrates direct external manipulation of intracellular content using nanostraws on the timescale of tens of seconds.

We used the delivery of GFP plasmid as a functional assay and a demonstration that a relatively large molecular weight species (~5000 bp construct) can be delivered with nanostraws (FIG. 2Q). GFP plasmid delivery was performed similarly to small molecule delivery, introducing 0.37 μg/μl plasmid in PBS into the microfluidic channel and allowing 24 hrs for cell uptake and expression. At the end of this period cells were fixed and imaged in a fluorescent microscope without replating. Since GFP-plasmid is not fluorescent, cells could be imaged directly on the nanostraw substrates. FIG. 2Q shows ~5-10% of cells located over the microfluidic channel are successfully transfected, while 0% of cells off the channel are affected. The spatial confinement confirms that nanostraws are necessary as membrane-penetrating conduits for intracellular delivery.

The efficiency of nanostraw-mediated delivery varies across different experiments and molecules. Small molecules, such as ions, are expected to be highly effective as they are small, have high diffusivity, and do not greatly adsorb to channel or straw sidewalls. Delivery of $Co^{2+}$ ions in in situ tests of GFP quenching was found to be over 70% efficient, indicating a majority of cells are penetrated by one or more nanostraws. The cell replating procedure used for long-term molecular deliveries resulted in lower yields of 20-30%. These measurements were skewed to lower values due to enhanced adhesion of cells interacting with nanostraws, such that a significant portion of cells resisted standard trypsinization procedures. In situ observation of GFP transfection resulted in yields of 5-10%. The efficiency of GFP expression relative to $Co^{2+}$ ion delivery is attributed to GFP plasmids having high surface affinity, lower diffusivity, and the additional biochemical translation and expression steps necessary. Delivery efficiency was also dependent on nanostraw density with maximum delivery observed at straw concentrations between $10^7$-$10^8$/cm$^2$. The ideal straw density is a compromise between two competing effects, as lower straw concentrations resulted in lower total molecular flux through the membrane, while very high nanostraw densities resulted in less frequent cell penetration, as cells appeared to rest on top of the dense nanostraw forest with a bed-of-nails effect.

Nanostraw Delivery Pathway

Figures 2R, 2S, 2T, 2U, 2V, 2W:
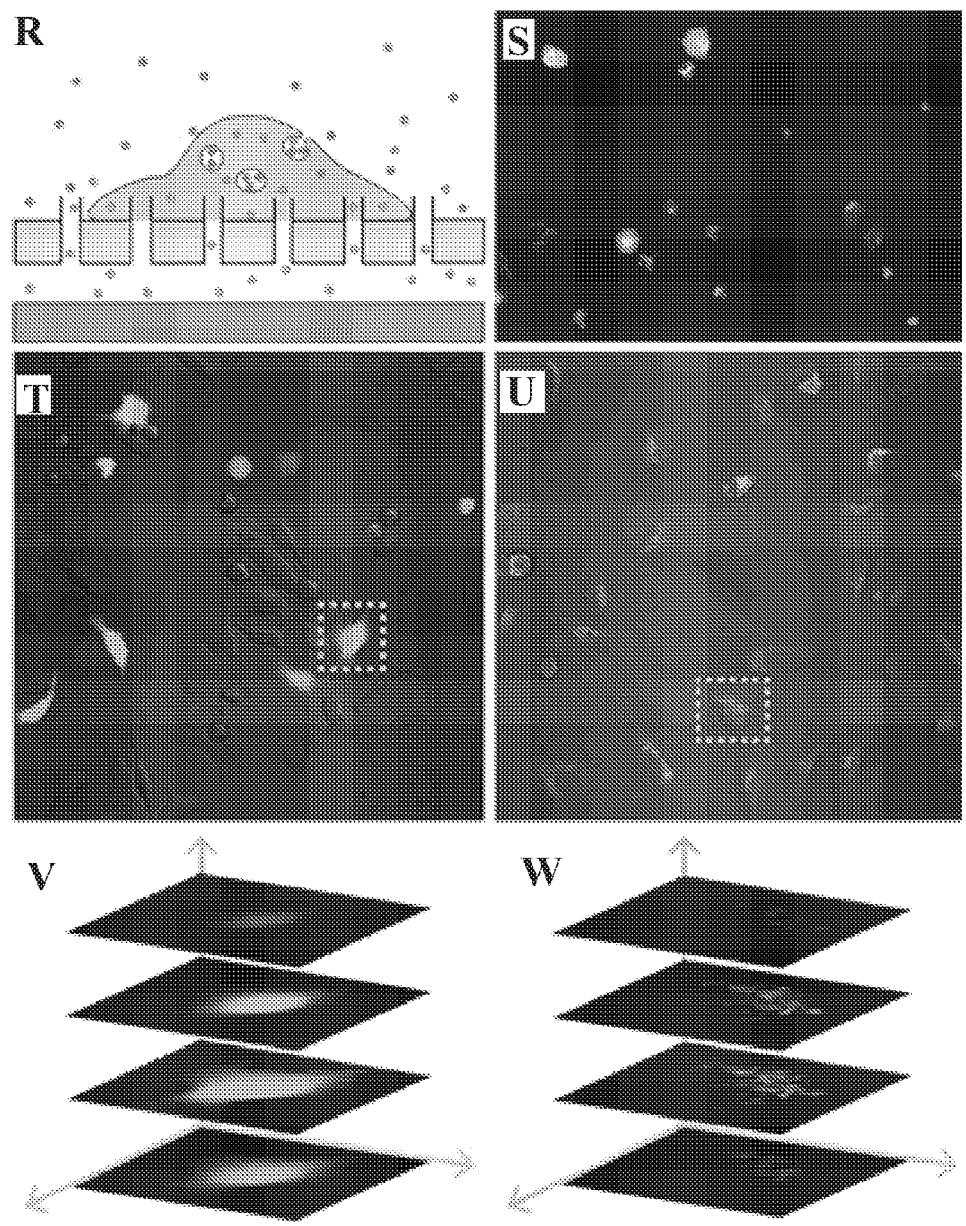
FIGS. 2R to 2W illustrate nanostraw-mediated and non-specific endocytotic dye delivery results in different localization patterns within cells.

We compared nanostraw-mediated dye delivery to dye uptake though other possible pathways to verify the role of nanostraws as membrane-spanning conduits. One concern is that nanostraws not penetrating into cells deliver molecules into the upper cell culture solution. Cells are well known to uptake molecules from solution through endocytosis {{55 Adler, Andrew F. 2010; 58 Verma, Ayush 2008}}, which can be difficult to distinguish from direct delivery (FIG. 2R). However, endocytotic dye uptake of membrane impermeable dyes is characterized by spatially confined points of fluorescence within the cell where dye is enclosed in discrete endocytotic vesicles, as opposed to uniform cytosolic distribution expected from direct delivery. To confirm that nanostraw-mediated dye delivery was not endocytotic, cells were imaged using confocal microscopy to determine the dye distribution (FIGS. 2S-2V). Alexa-Fluor 488-hydrazide dye (green) was delivered through the nanostraws, resulting in homogeneous cell-body fluorescence in selected cells (FIG. 2S). Simultaneous addition of Alexa-Fluor 568-hydrazide (red) into the upper culture well resulted in punctate vesicular fluorescence of red dye in all cells (FIG. 2S). These contrasting patterns of continuous and punctate fluorescence, as well as the difference in cell-to-cell staining (stochastic for nanostraws, consistent for endocytosis), highlight that extracellular dye uptake and nanostraw dye delivery operate on different principles. These delivery patterns were also preserved when nanostraw-mediated dye delivery and endocytotic uptake of dye were observed independently (FIGS. 2T and 2U). Confocal image slices showed uniform dye distribution throughout the entire cell bodies in the z-direction with nanostraw-mediated delivery, again in contrast to punctate fluorescence observed in cells cultured with dye-supplemented media. When dye was delivered to cells through track etched membranes without straws, the observed fluorescence pattern was also punctate, highlighting once more that nanostraws are needed to form direct conduits to the cellular interior.

The possibility that nanostraws puncture the cell membrane and allow extracellular molecules to diffuse into the cytosol must also be considered, as nonspecific leakage could provide an alternative pathway into the cell. {{89 Malboubi, M. 2009}} Leakage could occur at the nanostraw-cell interface, where the membrane must form a seal around the piercing nanostraw. This pathway is less likely due to the very significant difference between cells located over the fluidic channel and those over PDMS, even though they both share the same culture solution. This effect should have been especially dramatic for molecular ions due to their small size and high diffusion constants, however, GFP quenching by $Co^{2+}$ ions was strictly confined to cells directly over the channel, casting doubt on this mechanism.

mRNA Analysis of Cells on Nanostraws

Cells cultured on nanostraw platforms remained viable and proliferated based on optical microscopy and live/dead staining. More subtle changes in cellular behavior were probed by mRNA expression analysis {{69 Peng, Lily 2010}}. Gene chip analyses were compared between cells grown on nanostraw membranes and nanostraw-free membranes at time points of 2 hours, 3 days, and 5 days. Several cell functions were considered prime targets for genetic up-regulation among cells grown on nanostraws, including indicators of cell stress, endocytosis, and ion channel regulation. Cell stress is a common result of unusual culture conditions, including surface modification {{90 Gasiorowski, Joshua Z. 2010}}; up-regulated endocytosis is a proposed mechanism for impalefection of high-aspect nanowires {{55 Adler, Andrew F. 2010}}; and increased ion channel activity may be necessary to maintain the cell membrane potential if nanowire penetration results in ionic leakage {{92 Black, J. A. 1999}}. However, examination of genes associated with these cell functions {{93 Safran, Marilyn 2010}} reveals no expression changes greater than 1.21-fold (FIGS. 2X-2Z), considered statistically equivalent. This observation corroborates prior observations that high-aspect ratio nanostructure-cell interactions result in minimal cell perturbation. {{36 Shalek, Alex K. 2010}} Additionally, a Pearson correlation analysis of all 28,869 genes examined showed that in every instance, the differences between how long the cells were in culture was the most influential factor in mRNA expression variation, rather than the presence or absence of nanostraws.

Conclusions

The nanostraw platform leverages nanofabrication for in vitro biological studies by delivering membrane-impermeable species directly into cells with minimal perturbation. Unlike traditional delivery methods, nanostraw platforms combine long-term access, temporal control, low cellular disruption, and ready integration into microfluidic systems into a single device. These are important steps towards complete regulation and monitoring of internal cell dynamics. A wide range of current cell culture platforms can be powerfully augmented using nanostraw membranes, allowing biomolecule delivery in a massively parallel fashion over large areas. By non-destructively bypassing the cell's membrane barrier, nanostraw platforms may be able to alter the intracellular environment with the same degree of control that we currently exert over the extracellular solution, unlocking the full potential of engineered inorganic-cell communication.

Methods

Nanostraw Membrane Fabrication:

Track-etched polycarbonate membranes with either $10^6$, $10^7$, or $10^8$ pores/cm$^2$ (AR Brown-US) were coated with alumina ALD (TMA, $H_2O$, Cambridge Nanotech) using pulse cycles of the form a/b/c/a/b/c, where a is the precursor exposure time, b is the time that precursors were retained in the ALD chamber, and c is the $N_2$ purge time, each in seconds. To attain conformal coverage over high aspect ratio nanopores, a pulse cycle of 0.015/60/60/0.015/60/60 at 100° C. was used. Using a Plasma Quest reactive ion etcher, alumina was etched with a gas flow composition of 40 sccm $BCl_3$, 30 sccm $Cl_2$, and 5 sccm Ar at 300 Watts, and polycarbonate was etched with 30 sccm $O_2$ at 300 W. Samples were characterized using an FEI dual-beam SEM/FIB.

Microfluidic Device Assembly:

Microfluidic devices were produced using PDMS elastomer and crosslinker (Sylgaard 184, Dow Corning) in microfluidic molds photolithographically defined in SU-8 (Microchem) photoresist on 4" silicon wafers. PDMS molds and nanostraw membranes were treated with oxygen plasma at 100 W for <1 minute before device assembly. Before cell plating, the microfluidic devices were sterilized in oxygen plasma for <1 minute. An overnight incubation in polyornithine solution was used to prepare devices for cell culture.

Cell Culture Experiments:

HeLa and CHO cells were cultured in DMEM supplemented with 10% fetal bovine serum and 1% antibiotics at 37° C. and 5% $CO_2$. GFP plasmid (pAcGFP-Cl, Clontech) was used to transfect CHO cells using lipofectamine, and selected using media supplemented with 500 µg/mL G418. For GFP quenching, GFP-CHO cells were plated for 1 hour. The microfluidic channel was then perfused with 1 M $CoCl_2$ for 1 minute, and then 100 mM EDTA. For molecular delivery, microfluidic device channels were BSA blocked for 30 minutes and rinsed before the addition of Alexa-Fluor 488 Hydrazide dye to obtain a channel concentration of 100 µM in a channel volume of ~100 µL. Confluent cells were harvested and plated in microfluidic devices at ~$10^5$ cells/$cm^2$ in culture media without phenol red 30 minutes after dye delivery. For codelivery experiments, Alexa-Fluor 568 Hydrazide dye was delivered at 2 or 12 hours after plating by adding dye solution to the channel, resulting in approximate channel concentrations of 100 µM for both dyes. Experimental controls of cells cultured in media supplemented with 10 µM dyes occurred in parallel. At desired timepoints (4 and 24 hours), cells were washed with PBS, lifted using TrypLE, and replated. All solutions and reagents were obtained from Invitrogen. GFP plasmid was delivered through a microchannel at a concentration of 0.37 µg/µl in PBS. CHO cells were fixed in 2% glutaraldehyde and 4% paraformaldehyde at 4° C., stained with $OsO_4$, critical point dried, sputter coated with Au/Pd, and imaged using SEM.

Microscopy:

Epifluorescence microscope images were taken using the Axiovert 200M platform (Zeiss) with filter sets 10 and 0 (Zeiss) and Ex120 light source (X-cite). Confocal microscope images were taken using the TCS SPE platform (Leica) with excitation lasers of 400, 488 and 532 nm to image bright field, Alexa-Fluor 488-hydrazide dye, and Alexa-Fluor 568-hydrazide dye, respectively.

Gene Expression:

HeLa cells were seeded in 6 well plates on supported nanostraw substrates (100 nm diameter, 10 nm wall thickness, 1 µm tall, $10^7$ nanostraws/$cm^2$) and non-straw membranes. Cells were harvested at 2 hours, 3 days, and 5 days after plating, and were plated with an initial density so that each sample had ~$10^6$ cells at harvest. RNA was collected using a QIAGEN RNA Easy Plus Mini kit. RNA processing was performed at the Stanford Protein and Nucleic Acid Facility. RNA quality was analyzed with an Agilent Bioanalyzer QC, with each sample returning an RNA Integrity Number (RIN) of 10 out of 10. Gene expression was analyzed on Affymetrix GeneChip Human Gene 1.0 ST arrays.

References each of which is incorporated herein by reference

1 Loh, O. et al. Nanofountain-Probe-Based High-Resolution Patterning and Single-Cell Injection of Functionalized Nanodiamonds. Small 5, 1667-1674 (2009).
2 Chen, X., K is, A., Zettl, A. & Bertozzi, C. R. A cell nanoinjector based on carbon nanotubes. Proc Natl Acad Sci USA 104, 8218-8222, doi:10.1073/pnas.0700567104 (2007).

Example 2

Nanostraws for Direct, Fluidic, and Cellular Access

Figure 3A:
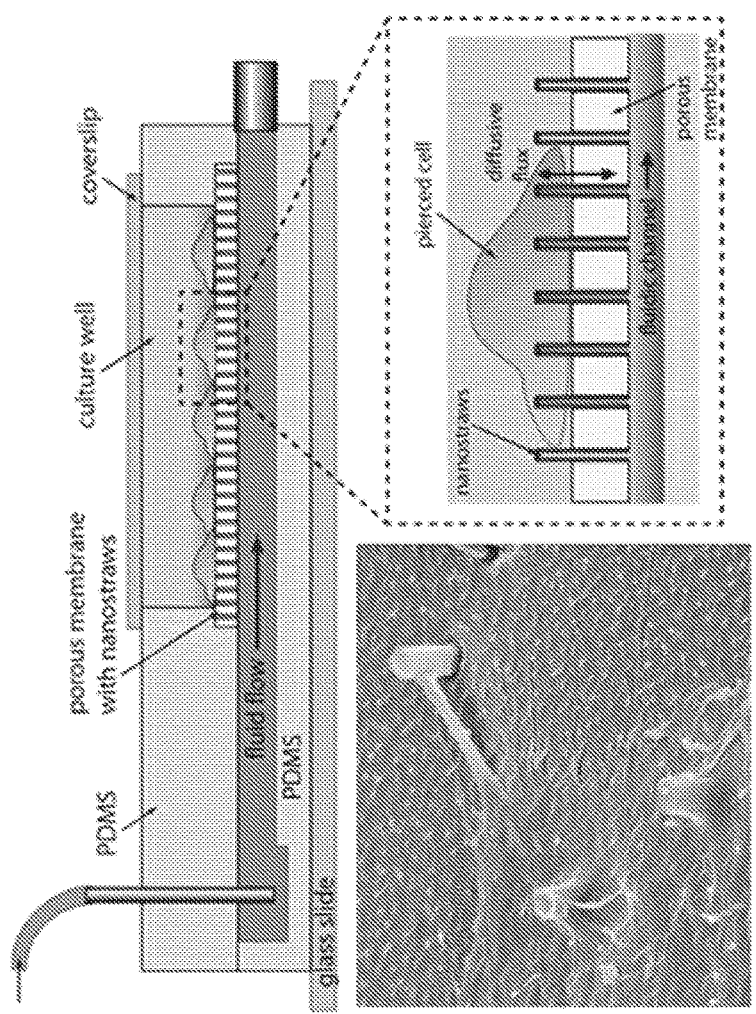
FIG. 3A illustrates an embodiment of a present disclosure.

Embodiments of the present disclosure use the idea of cells self-penetrating on nanowire arrays and extend it from bound signal delivery to soluble signal delivery with hallow nanowires, or nanostraws (See FIG. 3A). A fluidic subphase can be used for signal delivery or sampling. The high flow resistance of the membrane demonstrated previously provides a way to deliver to the cells without needing to control fine fluid volumes. Also shown in FIG. 3A is an SEM micrograph of a CHO cell cultured on nanostraws.

Figure 3B:
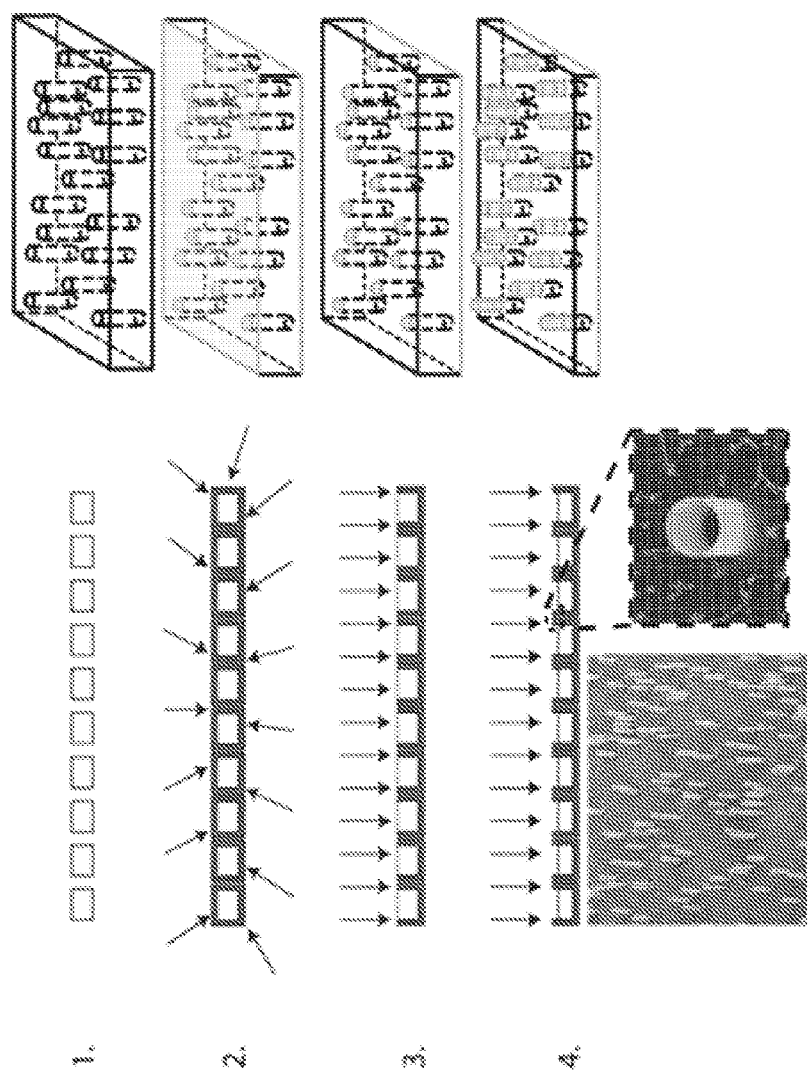
FIG. 3B illustrates a process flow for nanostraw fabrication.

FIG. 3B illustrates a process flow for nanostraw fabrication. Created on a nanoporous membrane template, the nanostraws are in registry with the membrane pores on the substrate. The aspect ratio of the nanostraws can be 1000:1 or more. The following steps are illustrative and are a non-limiting example of a process for nanostraw fabrication. Step 1: Track etched membrane. Step 2: conformal coating, ALD or electroless deposition. Step 3: Directional etch to remove coating from step two on top surface. Step 4: Directional, selective etch for membrane material. Also shown are nanostraw SEM micrographs created with this process flow.

Figure 3C:
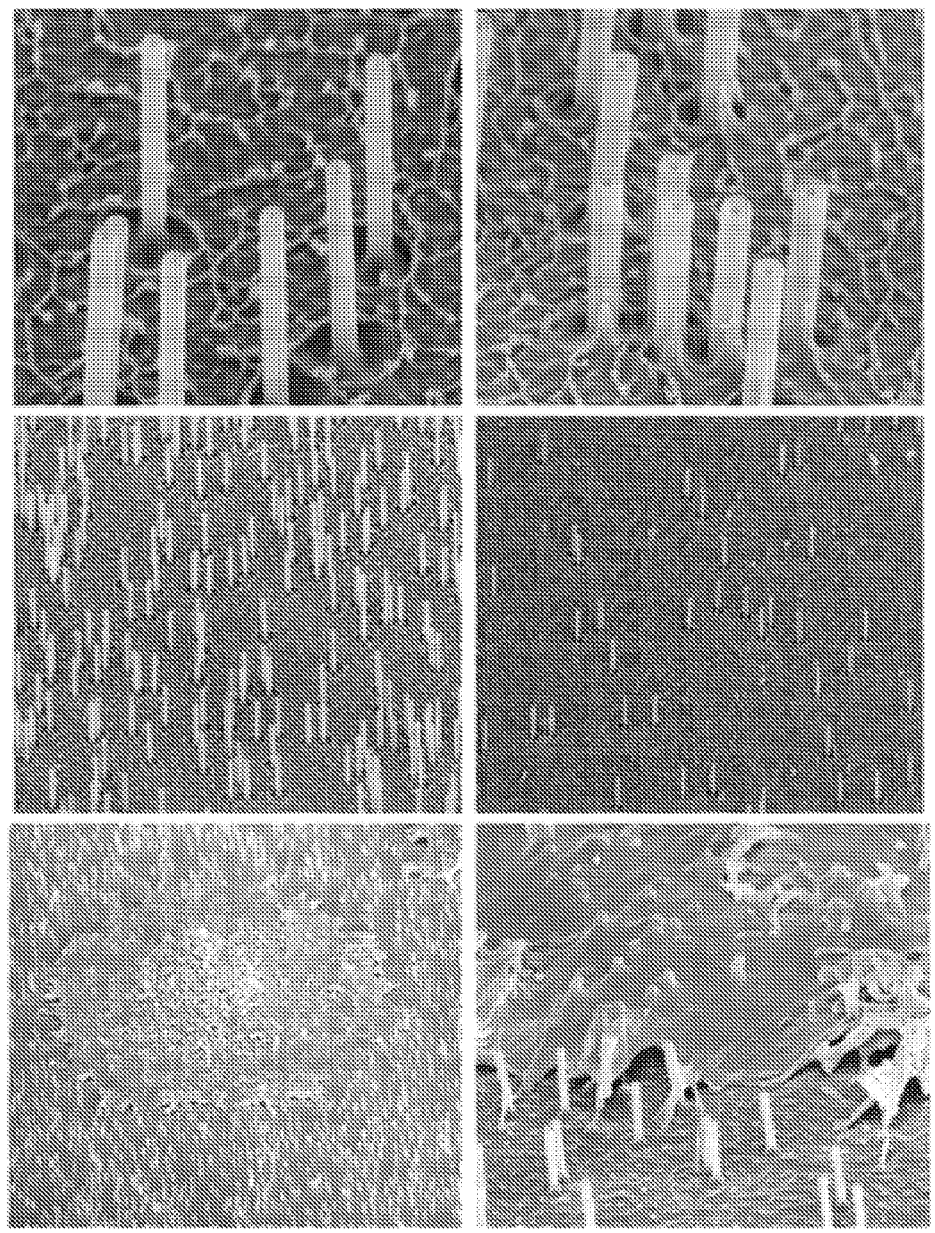
FIG. 3C illustrates 100 nm straws with 30 nm openings were used.

FIG. 3C illustrates 100 nm straws with 30 nm openings were used. These were created with $Al_2O_3$, are high quality, and can be grown in a variety of densities. Shown are $10^8$ and $10^7$ straws/$cm^2$. Straws have also been grown successfully at higher and lower concentrations, and at a variety of straw diameters and heights. Despite straw perturbation, cells culture readily on the nanostraw surfaces.

Figure 3D:
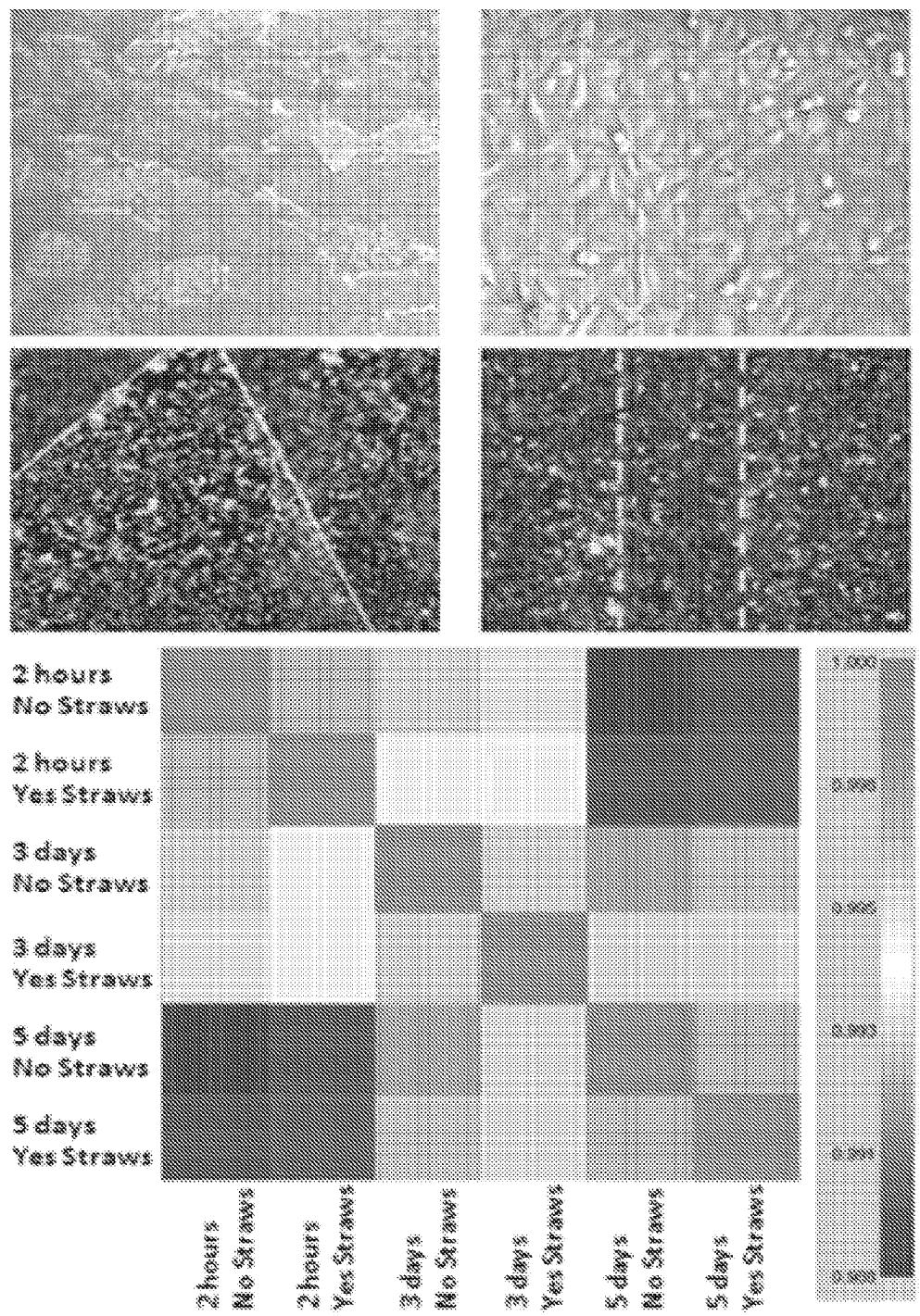
FIG. 3D illustrates a graph of cell viability is demonstrated on the straws.

FIG. 3D illustrates a graph of cell viability is demonstrated on the straws. At the top of FIG. 3D, SEM micrographs of well spread cell monolayers on a nanostraw forest are shown. Live dead tests shows no difference in viability between CHO cells cultured on the nanostraw membrane vs. on surface functionalized PDMS (middle left), or between supported (off the channel) and non-supposed (over the channel) nanostraws (middle right). At the bottom of FIG. 3D, a gene expression array shows no difference between HeLa cells grown on polycarbonate with and without nanostraws at timepoints 2 hours, 3 days, and 5 days after plating. The most disparate samples still have a Pearson correlation of 0.988. The comparison plot (bottom of FIG. 3D) shows that there is far more gene expression variation between different culture time points (i.e., 3 days vs. 5 days) than between any straw and non-straw samples at the same time point. Red indicates strong correlation in gene expression between samples and blue indicates a relative weak correlation.

Figure 3E:
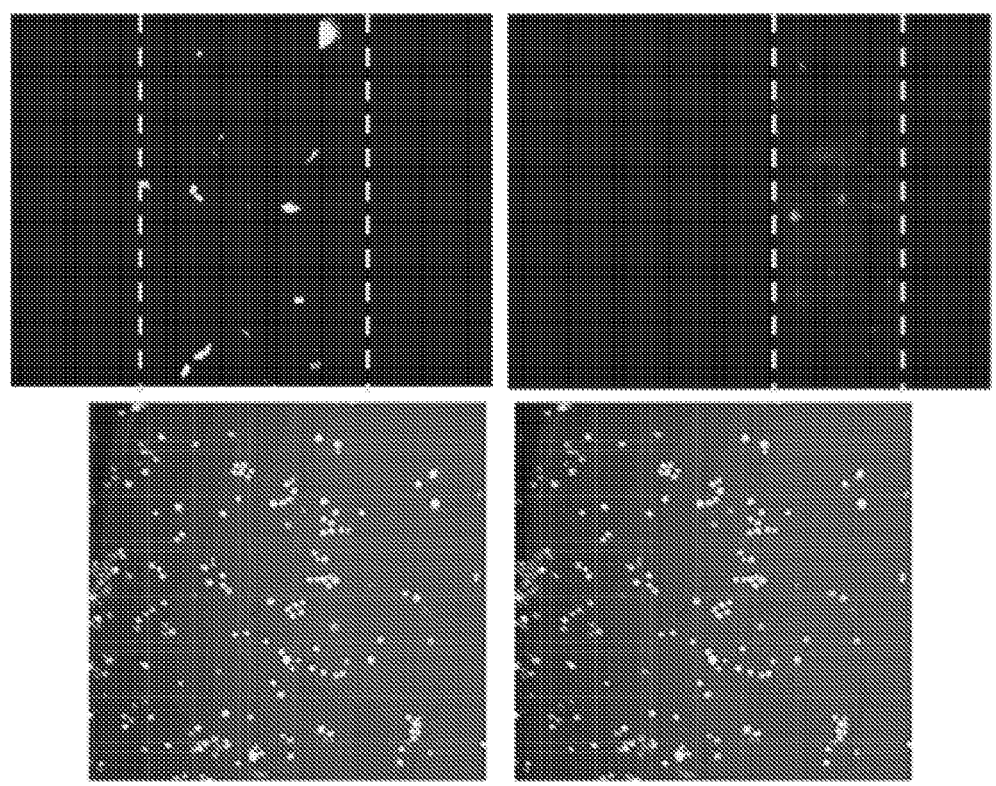
FIG. 3E illustrates the delivery of biomolecules to cells. At the top left of FIG. 3E, successful GFP transfection after three days from channel delivered plasmid at 1 µg/µl is shown.

FIG. 3E illustrates the delivery of biomolecules to cells. At the top left of FIG. 3E, successful GFP transfection after three days from channel delivered plasmid at 1 µg/µl is shown. Transfection percentage is typically 2-4% of cells. The top right of FIG. 3E illustrates the delivery of cell membrane impermeant fluorescent dye Alexa Fluor 350 hydrazide at 10 mM. The channel is quenched with $CoCl_2$, and delivery to several cells is evident on the channel top. The cells were then trypsinized and replated, and stained with a live/dead kit. Several cells dyed with hydrazide are evident at the bottom left of FIG. 3E. Each of these cells is alive (green, bottom right of FIG. 3E), and none exhibit a compromised membrane (red, bottom right of FIG. 3E). Very intense cell hydrazide delivery is ~5%, however, as many as 75% of cells above the channel show some hydrazide delivery.

Quantification of the fluorescent signal intensity in the hydrazide stained cells indicates the cells have less that 0.05% of the dye could expect from pure diffusion from the channel. This is equivalent to 1% of the straws providing access to the cells 5% of the time. However, not all of this loss likely occurs at the straw-cell interface, as experiments with dye diffusion through membranes with and without ALD alumina indicates a loss of diffusive flux much greater than is attributable solely to the constriction of the opening. Surface charge issues are likely a culprit (the Donnan effect).

Example 3

Non-Destructive, Long-Term Cytosolic Sampling of Rare Cells:

Embodiments of the present disclosure can be used to monitor cyctosolic protein and cytokine concentrations of rare cells over an extended period (7 days) and determine their response to therapy.

Analysis of intracellular protein and biochemical expression of rare blood-borne cells such as circulating tumor cells (CTCs) or cancer stem cells (CSCs) may be an effective means of detecting the particular cancer type and metastatic activity, allowing improved therapy selection and efficacy monitoring. Measuring the cytosolic contents of these cells is currently approached by either using membrane permeable dyes to label select structures, or by destructively lysing the cell and measuring the contents, as is performed for CCNE Aim N3.2.5.3. However, neither of these routes is entirely satisfactory for observing rare cell behavior and response to therapy. Dye labeling can only target a small number of species at one time, and the need for membrane permeability greatly limits the binding chemistry possible (for instance, antibodies cannot be used for selective attachment). On the other hand, cell lysis provides affords access to the entire cytosolic content, but destroys the cells for each analysis and provides information at a single time point. For very rare cells types such as CTC's and CSC's, it is generally not possible to conduct multiple lysing and analysis steps due to cell scarcity, and is complicated by heterogeneity in the population collected. This introduces difficulties in establishing protein concentration levels as a function of time and treatment, particularly if cells are at different points in their cell cycle or are from different populations. For instance, the Stanford CCNE and others are pursuing identifying the gene expression profiles for CTC's and establishing effective corresponding therapies. However, if the expression of each of these CTC's could be monitored over the course of time as different therapies are administered, a much more detailed and more reliable response of these cancers to therapy could be derived. This approach would mitigate the effects of cell-cycle and phenotypic differences by observing the cells over a much longer period, establishing an expression baseline for each cell before and after therapy at the single cell level. With single-cell level analysis, multiple cancers with different responsivities could be identified within the population, and individual treatment strategies applied. The key challenge is that access to the cytosolic contents is currently a destructive process.

Figures 4A, 4B:
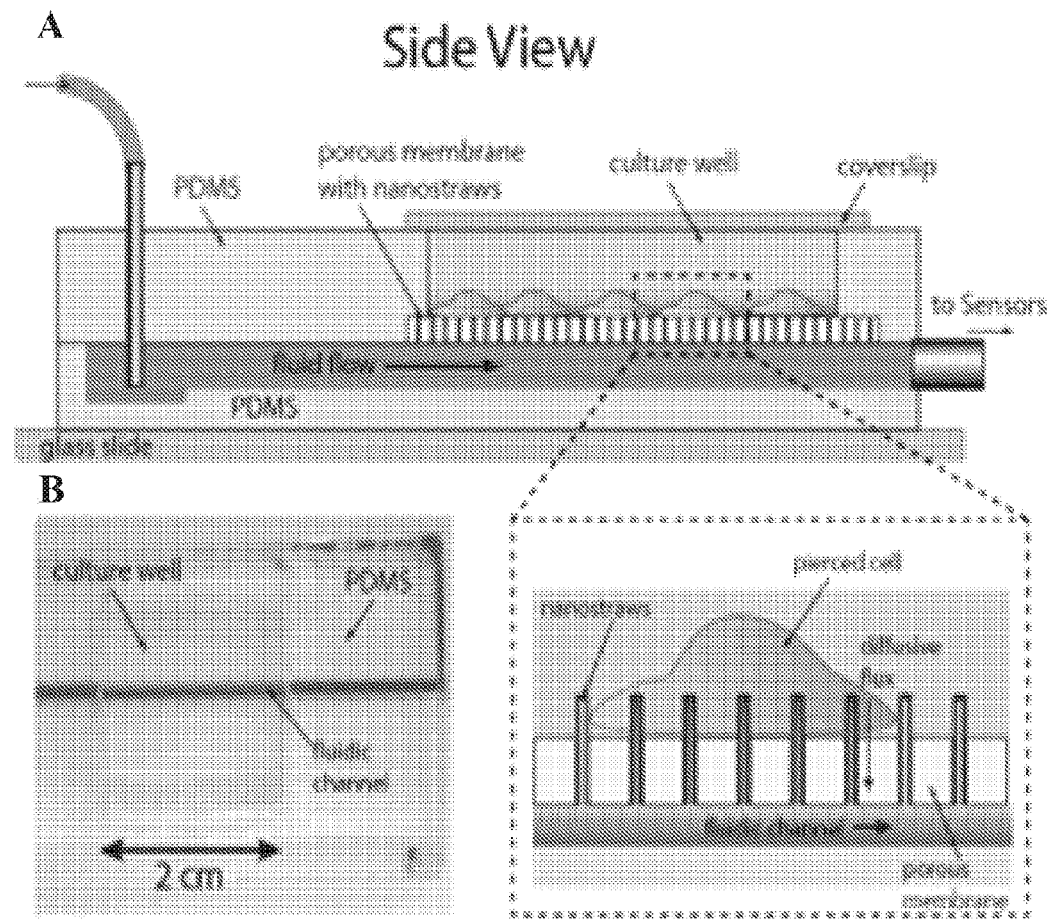
FIGS. 4A and 4B illustrate a diagram of the continuous-cytosolic monitoring device.
Figures 4C, 4D, 4E, 4F, 4G, 4H:
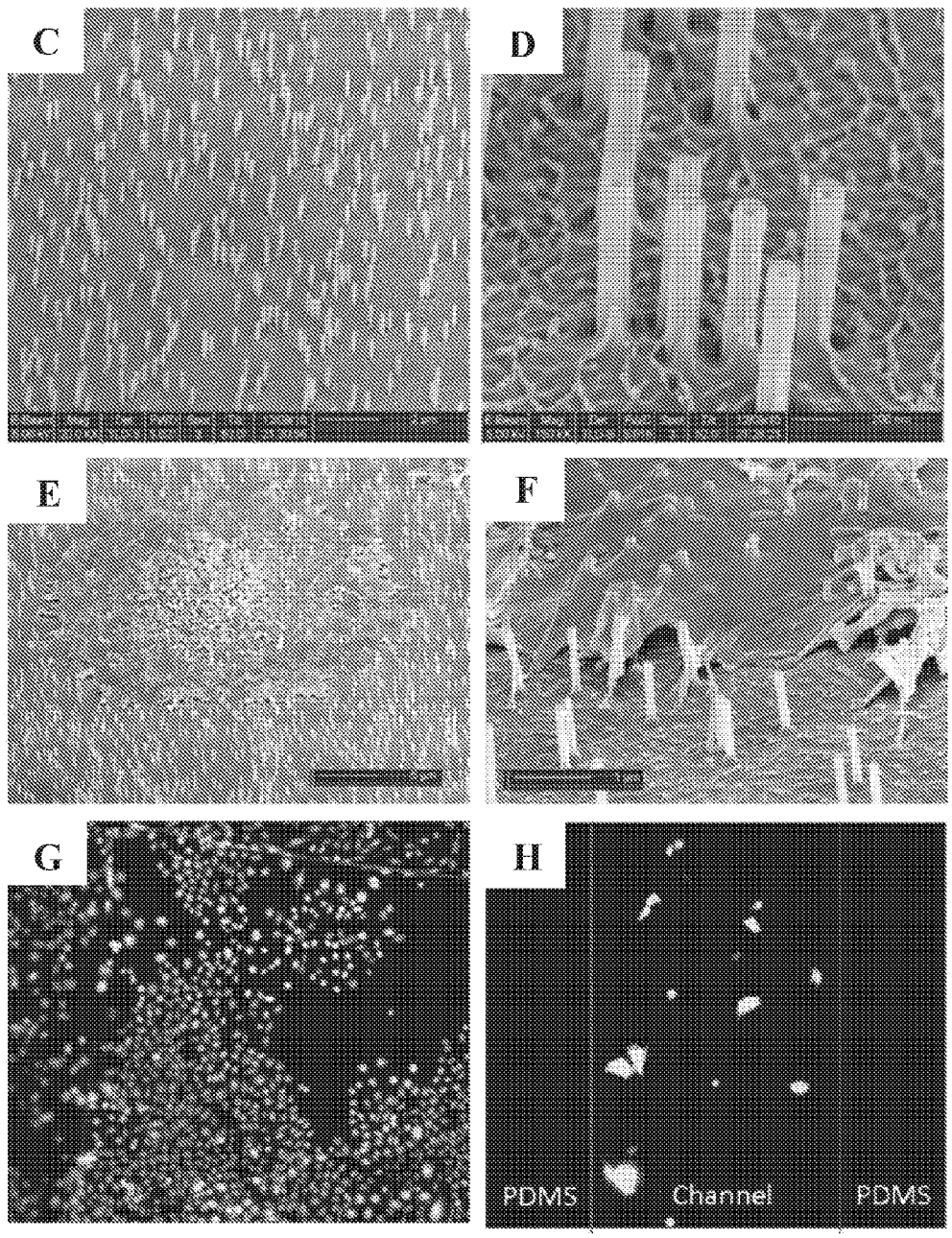
FIGS. 4C to 4H illustrate various images.

We propose to use a newly developed "nanostraw" platform to passively sample intracellular contents over the period of 7 days, using the Magneto-nanosensor technology developed by the CCNE at Stanford and the DEAL microfluidic antibody sensor developed at Caltech to measure the cytosolic concentrations (See FIGS. 4A and 4B). This platform directly pierces the cell membrane with ~100 nm diameter 'nanostraws', allowing cytosolic molecules to slowly diffuse out of the cell, but without rapid enough loss to cause cell death. We will use this platform to extract cytosolic proteins and deliver them to the already developed nanoscale detection schemes. For example, using the magnetic nanosensor chip we will measure cytosolic concentrations of tumor necrosis factor alpha (TNF-α), interleukin-1-alpha (IL-1α), interleukin-6 (IL-6), vascular endothelial growth factor (VEGF), Fibroblast growth factor 2 (basic) (FGF-2), Matrix metallopeptidase-9 (MMP-9), Granulocyte colony-stimulating factor (GCSF), and Eotaxin. PRDX6, Testican, Trop2, Claudin-1, B2M, and Serpin-1.

The principle barrier to directly measuring intracellular contents is the cell membrane, which forms a formidable barrier to transporting species across it. Recently however, a number of new materials have demonstrated the ability to non-destructively penetrate the cell membrane, including nanowires,[1,2] 'stealth probes'[3], and nanoparticles.[4] We have developed a new penetrating architecture, a 'nanostraw membrane' with microfluidic access that enables direct chemical/fluidic access into and out of the cell, but is small enough such that it does not perturb cell viability. The nanostraw platform is shown in FIGS. 4A and 4B. Here, tiny straws with controllable diameters from 50-200 nm are grown from a nanoporous membrane (such as Corning's Transwell track-etched cell culture membranes), typically 10-20 μm thick. This membrane is placed over a microfluidic channel, and sealed with a PDMS well on top (FIGS. 4A and 4B). This allows fluid contact through the nanostraws between the microfluidic channel and top of the nanostraw. Cells are then cultured on top of the membrane, where they are pierced by the nanostraws (if the nanostraws are small enough diameter, which appears to be ~100 nm). Contents between the cell and the microfluidic channel are now able to diffuse from one to the other, providing direct chemical delivery or cytosolic sampling of the cell. In many ways this resembles naturally occurring gap junctions between two cells, with the nanostraws in place of connexons. By properly tailoring the number and pore size of the penetrating straws, cell function is not inhibited.

This design has several critical advantages for enabling non-destructive, long term sampling of the cytosol, especially important for rare cells. First, the nanostraw dimensions can be easily modified such that it can penetrate the cell membrane directly, without causing lasting disruption of cellular function.[1,2] Secondly, the narrow fluidic orifice ensures that there is no net flow of fluid through the channel, which could change the pressure balance inside the cell. Instead, delivery and sampling is purely passive, through individual species diffusing through the channel. Third, the pathway from the cells to the analysis location is conducted purely microfluidically, reducing loss due to lysate handling. Fourth, the platform is amenable to scaling to different cell culture areas; from a single cell to a large-area culture well (~5×5 cm$^2$) so that a reasonable population of cells can be monitored simultaneously and statistics acquired, or single cell analysis performed.

Fabrication and preliminary cell culture results on the nanostraw platform are shown in FIGS. 4C-4H. CHO cells cultured on top of 100 nm-diameter nanostraws with 30 nm diameter pores spread well and grew to confluence. After 3 and 7 days cell viability was equal to control samples cultured on Transwell membranes without nanostraws, FIG. 4G, even though each cell was estimated to be pierced by ~300 straws (at a density of ~3 straws/μm$^2$). Access into the cell was demonstrated by adding GFP DNA plasmid into the fluidic channel, resulting in GFP expression by the pierced cells, and not those adjacent to them. These experiments demonstrate direct, non-destructive fluidic access through the cell membrane and extended cell viability.

Research Design

We will first demonstrate detection of intracellular proteins and cytokines using the nanostraw interface using non-rare cells, such as CHO cells. We will evaluate the lifetime of the cells on the platform and the intracellular contents over 7 days using the DEAL and magneto-nanosensor detection schemes previously developed within the Caltech and Stanford CCNE centers. These results will be compared and benchmarked against assays performed with standard lysates. Once the protocol has been established we will measure the contents of rare cells, such as CTC's collected from lung or ovarian cancer patients already being isolated in CCNE-T at Stanford. These results will be correlated with the magneto-nanosensor platform interrogation of CTC lysates. After establishing baseline function, we will apply selected therapies and monitor how cells respond. If successful, this direct sampling platform will provide time-resolved measurements of cytosolic species, enabling multiple experiments and time-points on a single population of cells. This project beautifully blends the ultra-sensitive techniques already developed through the two CCNEs with a revolutionary technique for long-term non-perturbative cytosolic sampling.

Methods

Cytosolic sampling will proceed as diagrammed in FIG. 4A. CHO cells are cultured to confluence on top of the nanostraw substrate, which has a microfluidic channel running beneath. Cytosolic proteins and small molecules will diffuse through the nanostraw into the fluidic channel. These species will be detected by either (a) flowing magnetic nanoparticles with capture agents through the channel, which are transported into a microfluidic tube to the magneto-nanosensor developed by the Wang group, or (b) flowing the solution into the DEAL antibody array chip with antibodies targeted to the species of interest, developed by the Heath group at Caltech. These results will be compared to standard lysate assays of cells cultured on Transwell membranes without the nanostraws.

Estimates of the signal concentration in the fluidic analysis chamber can be made by calculating the diffusive current of molecules from the cell cytosol through the nanostraws. For a molecular species of concentration Co in the cell and diffusivity D, coupled with a nanostraw of pore radius r and length L the molecular current per straw is given as (FIG. 4I):

$$I = C_0 \left[ \frac{4\pi D r^2}{\pi r + 4L} \right]$$

Figures 4I, 4J:
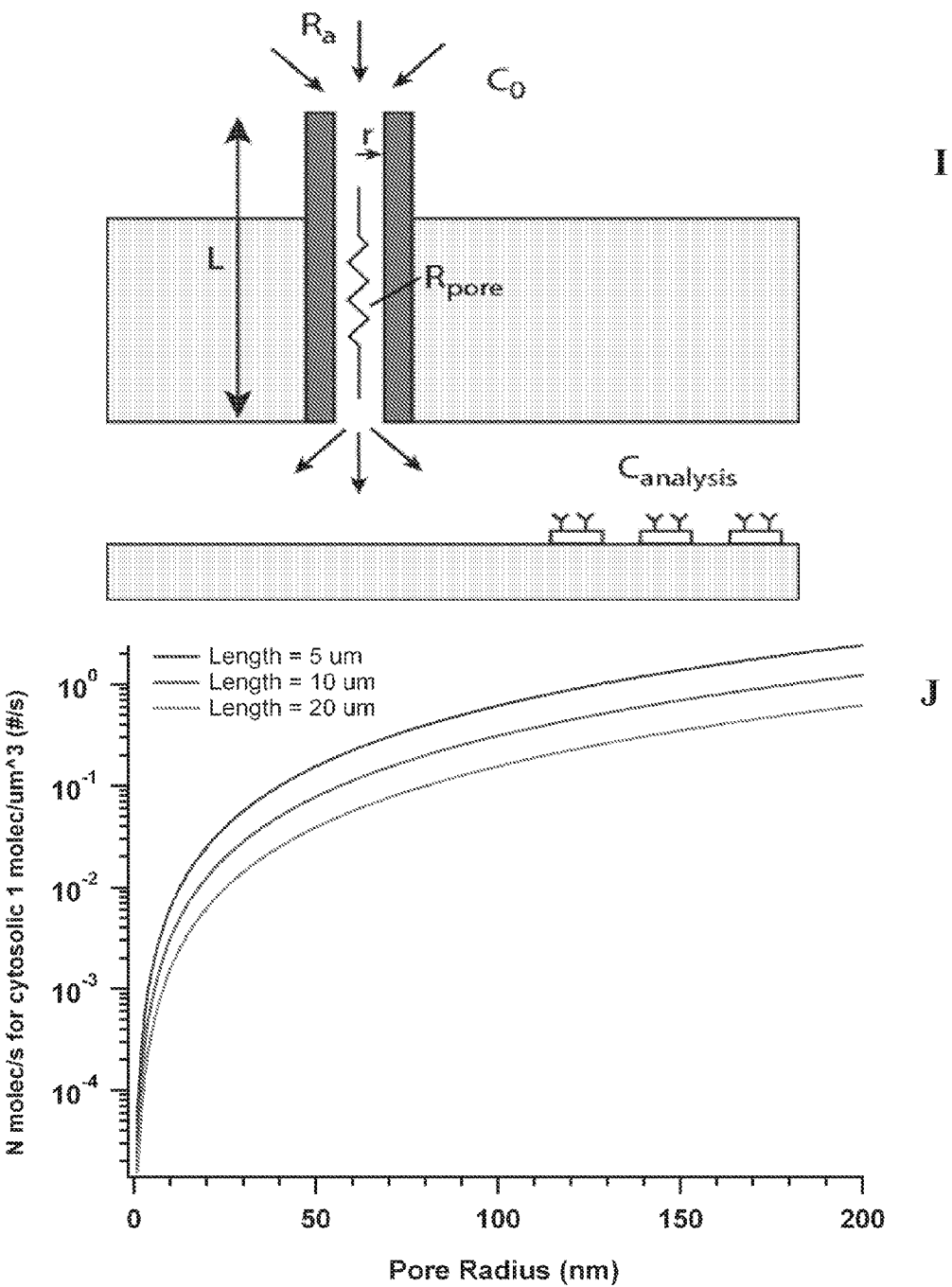
FIGS. 4I and 4J illustrate the rate of molecular diffusion through a single nanostraw.

Calculations for current from a 30 nm pore radius, 1 molecule per $\mu m^3$ concentration and different membrane thicknesses are shown in FIG. 4J. These show that for cellular abundances of ~$10^4$/cell approximately 100 molecules will diffuse into the analysis channel per hour for each nanostraw. If the analysis channel (equivalent to the amount of fluid that will be injected into the measurement chips) is 200 µm wide by 10 µm high and 100 µm long, this corresponds to a concentration of ~1 fM per nanostraw. For ~300 nanostraws per cell, this is roughly 300 fM, which should be readily detectable by DEAL or GMR sensor platforms. The pore diameter and membrane thickness will be synthetically modified to increase signal as necessary.

References each of which is incorporated herein by reference

1. Shalek, A. K. et al. Vertical silicon nanowires as a universal platform for delivering biomolecules into living cells. Proc Natl Acad Sci USA 107, 1870-1875, doi:10.1073/pnas.0909350107 (2010).
2. Kim, W., Ng, J. K., Kunitake, M. E., Conklin, B. R. & Yang, P. Interfacing silicon nanowires with mammalian cells. J Am Chem Soc 129, 7228-7229, doi:10.1021/ja071456k (2007).
3. Almquist, B. D. & Melosh, N. A. Fusion of Biomimetic 'Stealth' Probes into Lipid Bilayer Cores. Proc. Natl. Acad. of Sci. of the USA 107, 5815-5820 (2010).
4. Verma, A. et al. Surface-structure-regulated cell-membrane penetration by monolayer-protected nanoparticles. Nat. Mater. 7, 588-595, doi:10.1038/nmat2202 (2008).

Example 4

Introduction

The extracellular microenviroment is of critical importance in determining cell fate, including replication,[1-3] migration,[2] and differentiation.[1,2,4,5] Soluble chemical signals such as growth factors[5,6] serve key purposes in the cellular interactome by directing cell function. For example, chemokines released from damaged cells recruit and stimulate leukocytes as part of the wound healing response,[6] nerve growth factor (NGF) sources direct neurite outgrowth direction[7], and chemical signals in the stem cell niche regulate division type and determine differentiation pathways.[1].

Mimicking a cell's microenvironment requires controlling the chemical composition on cellular (micrometer) lengthscales. This is an area of great interest for developing lab-on-a-chip technology, integrated microfluidics, and regenerative medicine techniques.[8] Typically, these delivery devices fall into two categories: passive delivery systems where the mechanism is diffusive, or active delivery systems which rely on fluid flow.[9] The active species in passive delivery materials are often pre-loaded into a material with known diffusion characteristics,[10-12] or incorporated into a degradable polymer.[11-14] These methods are constrained by fixed and predetermined release rates and doses, as well as limited temporal control.

Active delivery systems, commonly implemented with microfluidics, use fluid control to deliver signals with more complex spatial and temporal patterns. However, signal delivery with fluid flow directly over the cells creates numerous artifacts. Shear forces exerted by the fluid affect the direction of cellular chemotaxis,[15] while influencing cell differentiation,[16] alignment,[17] and activity.[18] Fluid motion can also disturb non-adherent cells such as embryoid bodies,[19] and remove autocrine and paracrine signals released from cells, further distorting the natural cellular environment.[20] The removal or confinement of exogenous cell signals has a major influence on many cell cultures, such as the lower proliferation rates observed for fall armyworm ovarian cells (Sf9) cultured in microfluidic channels versus traditional culture environments.[3] The same event occurs in vivo, where the spatial constriction of sonic hedgehog homolog (SHH) modulates hair follicle formation in the follicular niche.[1]

In microfluidic systems a chemical gradient is a popular signal pattern to present to cells, either within a flowing fluidic channel or a flow-free architecture.[9] Flow-free gradients are generally created though purely diffusive mechanisms between two sources of different chemical concentrations. The sources may be continually replenished flow channels[19,21,22] or large reservoirs[20,23]. These methods require fluid flow restriction between the sources and the gradient area, typically by porous membranes,[20,24] hydrogels,[21,23] microjets,[19,22] and geometrical restrictions.[25-26] However, the time required to establish a stable diffusive gradient scales as the square of the distance between the sources, thereby limiting the size of the cell culture area to sub-millimeter length scales.

In this Example we present a new large-area device for spatial and temporal control of chemical signal patterns using diffusive delivery, eliminating complications with fluid flow and allowing one to rapidly alter solution concentrations over large areas. This device (FIGS. 5A and 5B) uses a standard microfluidic platform as a base and chemical signal source, while a nanoporous membrane serves as a cell culture platform as well as a partition from the fluid flow of the microfluidic channel. Similar nanoporous membranes suspended over solutions have been successfully used as cell culture platforms in a variety of applications, as exemplified by "Transwell" devices.[9,24,27] The chemical delivery timescale is dictated by the time needed to diffuse through the membrane rather than across the cell culture surface, reducing the time needed to establish a channel sized pattern, such as a chemical gradient, from hours to minutes.

Net fluid flow through the membrane into the culture well is prevented by the high fluidic resistance of the channels and by completely filling the culture well and sealing the top. The incompressibility of water prevents additional fluid from flowing into the chamber, although molecules are still able to diffuse across the membrane. In our experiments using membranes with 30 nm diameter pores, fluidic resistance alone appeared sufficient to prevent net fluid flow, as signal flux was indistinguishable between sealed and unsealed reservoirs. Small molecule net diffusion rates through the membrane were measured to be $4.06 \times 10^{-5}$ mol/hr/cm$^2$ for a 1 M source, in agreement with finite element simulations. Lateral chemical gradients were easily and quickly achieved using a gradient mixer upstream of the microfluidic channel under the cell culture area, observed by differential cell staining In addition, chemical pulses could be delivered by flowing alternating volumes of the signal and buffer solution.

Materials and Methods
Device Design and Microfabrication

Figures 5A, 5B:
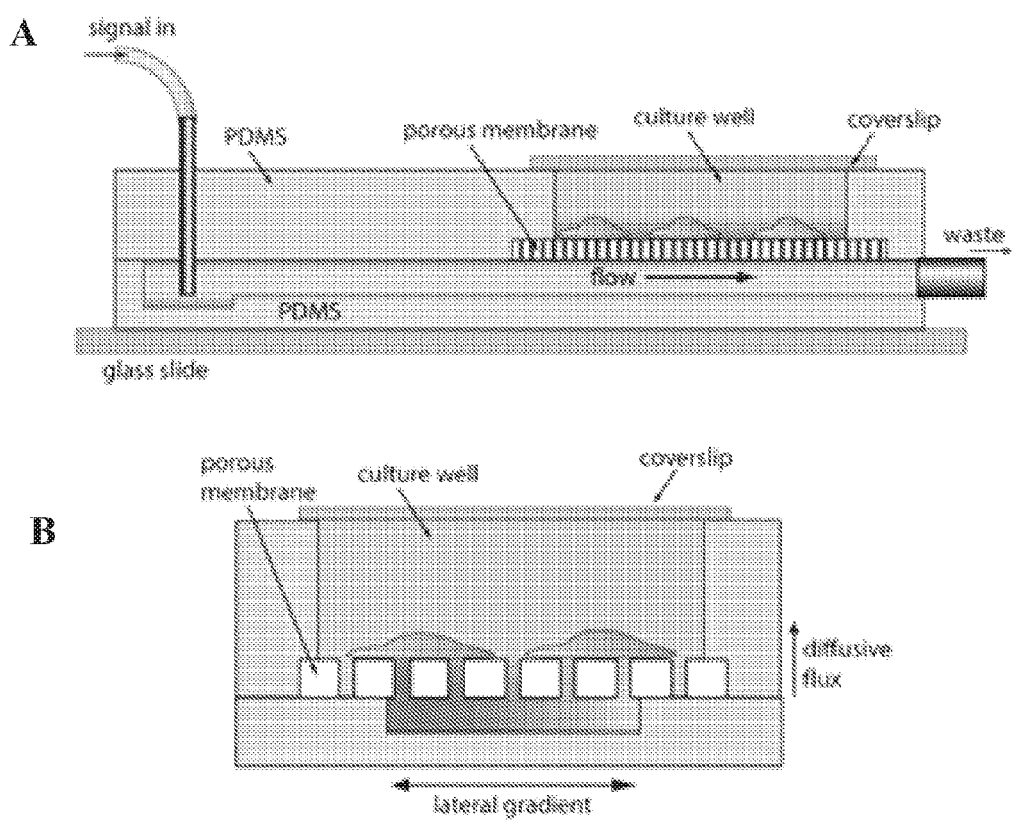
FIGS. 5A and 5B illustrate a microfluidic membrane-based device design viewed from the side (FIG. 5A), or end-on (FIG. 5B, not to scale). The porous membrane is sandwiched between two PDMS layers, the bottom layer containing the microfluidic flow lines, and the top layer the culture well. The cells grow on the membrane surface. The culture volume can be sealed to prevent net fluid flow through the membrane, although experiments show that this is unnecessary.
Figure 5C:
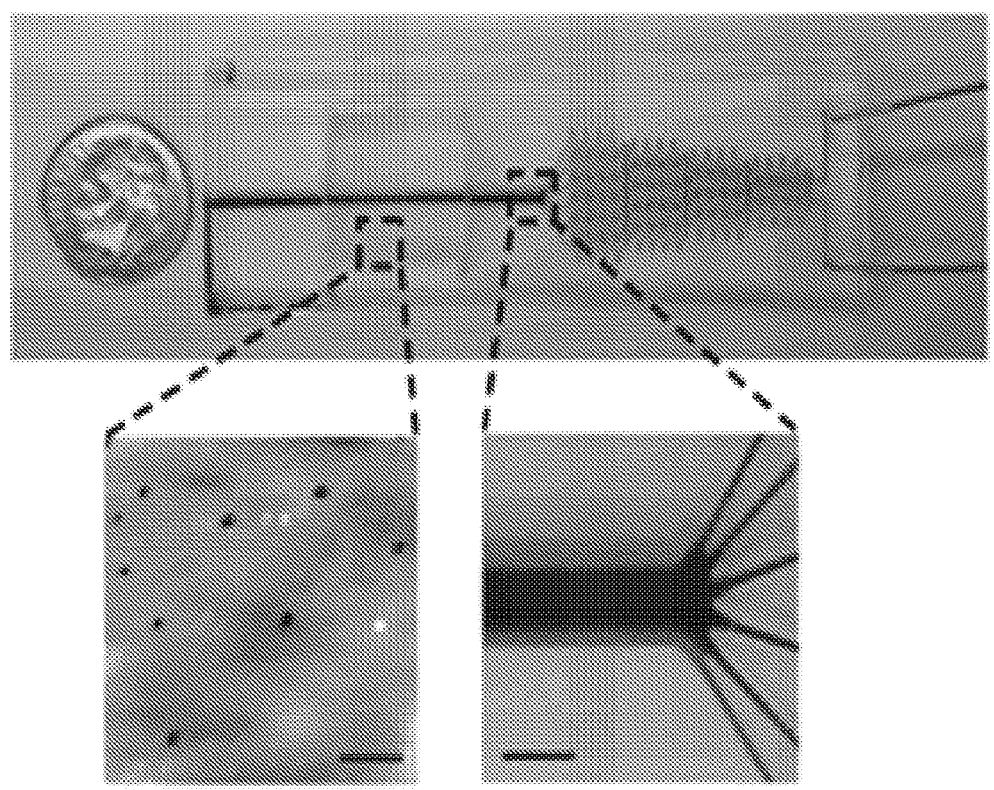
FIG. 5C illustrates an example device used in this paper is shown next to a US dime for size comparison. A gradient mixer is used to create a color gradient that is maintained along the 1000 µm-wide channel under the cell culture area with a volumetric flow rate of 1 µl/min (bottom right, scale bar 1000 µm). An AFM image of the track etched polycarbonate membrane is depicted (bottom left, scale bar 200 nm).

The functional device consists of a nanoporous polycarbonate (PC) membrane sandwiched between two layers of PDMS (FIGS. 5A and 5B). The assembly is then mounted on a glass coverslip or microscope slide backing for stability. PDMS and PC are both transparent, allowing the device to be imaged using both inverted and transmitted light microscopy. The bottom PDMS layer contains the microfluidic channels, and is thin enough (<500 µm) to image with an inverted microscope. A device with a lateral gradient mixer is illustrated in FIGS. 5A and 5B[28].

Construction

A negative master mold for the microfluidic channels was created using standard photolithography techniques in SU-8 negative photoresist (MicroChem, Newton, Mass.) on a four inch bare silicon wafer. A similar mold was created for the top PDMS layer, which details device boundaries, the culture well area, and micro-fluidic input port locations. Pretreatment of the device molds with a 15 minute FOTS (Fluoro-Octyl Trichlorosilane, Gelest Inc., Morrisville, Pa.) vapor exposure was used to facilitate the removal of cured PDMS device layers. Sylgard 184 (Dow Corning, Midland, Mich.) PDMS was mixed together thoroughly and degassed per manufacturer's instructions and used to cast the device layers on the photopatterned wafers. The elastomer was cured at 80° C. for 45 minutes. Normal curing recipes call for a longer curing time or higher temperatures, but slightly undercrosslinked PDMS allows for better bonding between device layers. By mixing the PDMS in a 15:1 pre-polymer to hardener weight ratio instead of the prescribed 10:1 weight ratio, the mixture becomes hardener deficient, which similarly aids in bonding device layers.

After the wafer molds were allowed to cool, PDMS layers were peeled from the molds and trimmed to size. The cell culture well was cut into the top PDMS layer, and the microfluidic inlet ports were punched. PDMS mating surfaces were cleaned, first using scotch tape to remove stray particles, then a UV-ozone cleaning treatment (Jelight Company, Inc. Irvine, Calif.) for 5 minutes. The nanoporous PC membrane (KN3CP04700, GE) was treated with oxygen plasma at 50 W for 30 seconds (SPI PlasmaPrep II, SPI supplies, West Chester, Pa.). Surface treatment of PC membranes was incompatible with UV-ozone cleaning as significant UV exposure degraded the polycarbonate.

A thin layer of hardener from the Sylgard 184 elastomer kit was used to bond the PDMS layers and the PC membrane. This was most effectively done through spin coating a thin layer of hardener on a coverslip and inking the PDMS surfaces. Depositing the hardener directly on the nanoporous membrane resulted in pore blockage, so the hardener was applied to the PDMS surface only. After the PDMS surfaces were treated with the hardener, the membrane was placed on the lower PDMS surface, then sandwiched with the top PDMS layer (FIGS. 5A and 5B). The assembled devices were cured at ~75° C. for 12 hours or longer. After the device was cured, it was mounted on a glass slide or coverslip for additional stability.

Fluid input into the microfluidic device was controlled with a gaseous pressure source and regulator for time transient experiments, while a syringe pump was used for gradient assays.

Cell Culture

Prior to cell plating, the microdevices were surface functionalized and sterilized with a 30 second oxygen plasma treatment at 100 watts. Chinese hamster ovary (CHO) cells were cultured and seeded in microfluidic devices in high glucose Dulbecco's modified eagle medium supplemented with 10% fetal bovine serum and 1% penicillin-streptomycin-glutamine (Invitrogen, Carlsbad, Calif.) at 37° C. and 5% $CO_2$. Cells in microdevices were allowed to grow to up to a monolayer in density and fixed in 70% methanol for 30 minutes. Fixed cells were stained using ethidium homodimer and SYBR Green I (Invitrogen), prepared in serum free media at 100 µM and 100× concentrations, respectively. Alexa-Fluor 350 hydrazide (Invitrogen) at 10 µM was used as an indicator dye in both solutions. The dye solutions were loaded into syringes and connected via tubing to the device input ports, and a syringe pump was used to establish a total flow rate of 2 µl/min. After 10 minutes the tubing was removed from the device and the flow channels and cell culture well were flushed with PBS. PC membranes used for cellular experiments had a pore diameter of 750 nm and a pore density of 106 cm-2 (AR Brown-US, LLC, Pittsburgh, Pa.).

Image Capture and Analysis

Micrographs were taken using a fluorescent inverted microscope (Zeiss, Oberkochen, Germany). Oregon Green dye (Invitrogen) was used for gradient and pulse quantification. SYBR Green I and Oregon Green dyes were imaged using Zeiss filter set 10 (excitation 470, emission 540), ethidium homodimer was imaged using Zeiss filter set 00 (excitation 546, emission 590), and Alexa Fluor 350 hydrazide was imaged using Zeiss filter set 49 (excitation 365, emission 397). Image intensity profile plots were analyzed using ImageJ software from the National Intitutes of Health. Nanoporous membrane characterization was performed with a FEI XL30 Sirion scanning electron microscope (FEI, Hillsboro, Oreg.).

Diffusion Rate Characterization

The diffusive flux through the nanoporous membrane was assessed by measuring the concentration of Allura Red dye (FD&C Red 40, McCormick & Company, Inc., Sparks, Md.) within the cell-culture chamber as a function of time. The device chamber was filled with deionized (DI) water and sealed with a coverslip and vacuum grease, and concentrated dye was applied via microfluidic inputs. The dye concentration in the chamber was measured at sequential intervals into both sealed and unsealed (no coverslip) reservoirs. Channel flow was maintained at 1 µl/min with a syringe pump (New Era Pump Systems, Inc., Wantagh, N.Y.). Solution from the culture chamber was analyzed with a spectrophotometer (Ultraspec 2100 pro, GE Healthcare, Chalfont St. Giles, United Kingdom) in absorption mode at 504 nm.

Fluid Flow Simulations

Finite element models (Comsol, Stockholm, Sweden) were used to simulate species diffusion from the main channel, through the membrane, and into the cell culture chamber. The model was a two-dimensional cross section of the culture well and microchannel with pore spacing adjusted to preserve the correct membrane pore density. The time-dependent diffusion equation was solved to obtain concentration profiles and the net flux of species into the cell chamber. Walls and membrane surfaces were treated as zero-flux boundaries, with the concentration in the microchannel held constant. All other concentrations were normalized to the microchannel. The polycarbonate membranes have a measured pore density of 4.3 pores/µm$^2$, a measured membrane thickness of 10.7 µm, and a published pore size of 30 nm (+0, −20%) (KN3CP04700, GE Osmonics). A pore size of 27 nm was used for the FEM model calculations.

Results and Discussion

The key feature of this device is the ability to deliver signals vertically into a large-area culture well through a nanoporous membrane. FEM simulations of purely diffusive delivery show a flux nearly identical to the empirical data, indicating that diffusion is the primary delivery mechanism. Additionally, delivery rate experiments show the same flux into both sealed and unsealed reservoirs, indicating that flow into an open chamber is also diffusive. An analytical model based on diffusive delivery, and verified by FEM and empirical data, quantifies the relations between device design and performance parameters. This enables a priori evaluation of new device designs, and is necessary to evaluate some designs too large or complex to evaluate through FEM. Delivery of signals from a lateral gradient in the channel is simulated through FEM, and is demonstrated by staining cells with dye gradients. Temporally pulsed signals were achieved by alternating signal and buffer solutions in the channel. Evaluation of cell staining from a step-function profile demonstrated signal delivery in under 45 s, and complete nuclear staining in under 6 min, highlighting the device's ability to rapidly introduce a static gradient over large areas.

Modeling Chemical Delivery Through the Membrane

The rate of chemical species delivery from the flow channel to the cells was modeled as a diffusive flux through the membrane, which depends on the membrane porosity and thickness. The characteristic time for a small molecule (D=5×10$^{-6}$ cm$^2$/s) to diffuse across a single 10 µm channel (the thickness of the nanoporous membrane) from a simplistic one-dimensional diffusion model is ~50 ms, yet this will be modified by the presence of a number of channels in parallel within the actual membrane.

Figure 5D:
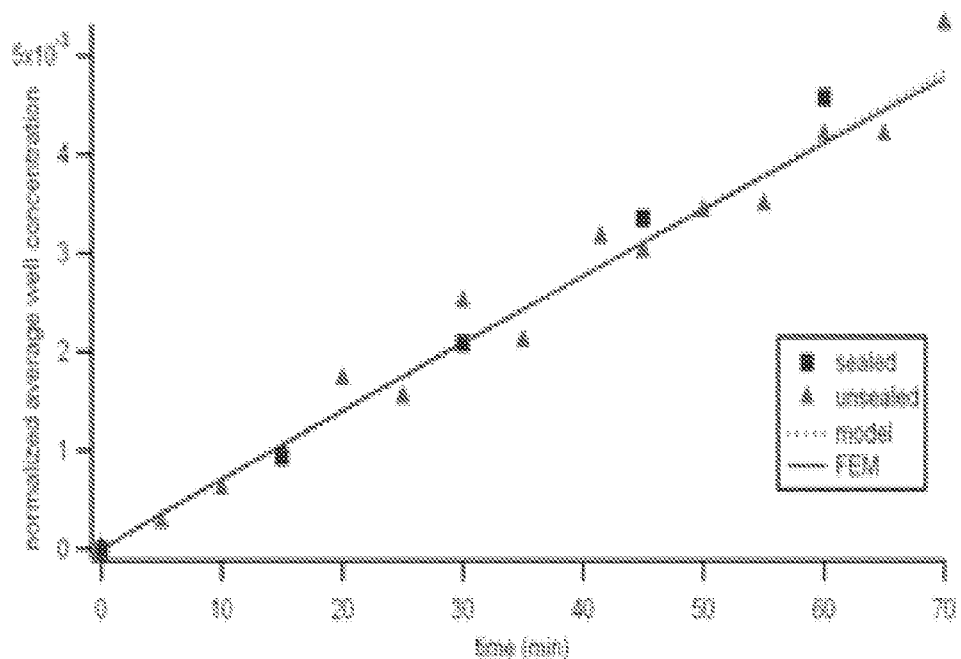
FIG. 5D illustrates an empirical data are shown with two different models for increasing concentration in the culture well over time. The analytical model fit is nearly coincident with the data line of best fit, after fitting for a. The device used for this trial had a 1000 µm wide channel, and a culture well of dimensions 16.8×16.3 mm with a total volume of 1.25 mL. The length of the channel in contact with the culture volume was 16.3 mm for a total channel contact area of 0.164 cm². The triangles are culture well samples analyzed in a spectrophotometer at various time points with the chamber sealed, allowing only diffusion to transport the dye through the membrane. The squares are samples run with an unsealed chamber, allowing for the possibility of pressure driven flow through the membrane. At a volumetric flow rate of 1 µm/min, the same rate used to maintain a flow channel gradient in FIG. 5C, the flow rates through the membrane were virtually identical in the sealed and non-sealed devices ($R^2=0.973$), indicating that the primary transport mechanism of dye through the membrane was still diffusion in an open chamber. The black line represents the average well concentration vs. time as predicted using a COMSOL finite element simulation. The simulation assumes that diffusion is the only transport mechanism through the membrane. The green dashed line shows the average well concentration vs. time as predicted using the analytical model (Equation 1) with $\alpha=2.5$.

Using SEM measured pore density and membrane thickness with published average pore size as parameters, and assuming a fixed dye concentration in the microchannel, finite element modeling agreed well with the experimental data (FIG. 5D). The bulk concentration in the cell chamber increased linearly with time, with the slope determined by the flux through the membrane. On first-order the flux is directly related to the channel-membrane area and porosity. A linear fit to the empirical data and a linear fit to the FEM simulation through the origin have a relative difference in slope of 3.5%, well within the error of the pore size and density measurements. Calculations reveal approximately how quickly cells experience the chemical signal. For example, the chemical concentration 1 µm above the culture surface is predicted to reach 1% and 10% of the channel concentration within 5 seconds and 10 minutes, respectively (not accounting for fluid perturbations due to the cells themselves). This contrasts with the average culture well concentration after 10 minutes, which would be approximately 0.03% of the maximum channel signal, illustrating the localization of signal delivery.

The modeled flux matched experimental results with a significance level of α=0.05. This indicates that even with an open culture chamber the primary transport mechanism through the membrane is diffusion rather than net flow. A very small flow cannot be ruled out, even in the sealed case, due to elastic deformation or fluid leakage into the PDMS, which would invalidate the assumption of fluid incompressibility. However, these effects are likely quite small, and the high measured fluidic resistance of 6.9×10$^{-7}$ s/µm$^3$ agrees well the FEM value of 7.0×10$^{-7}$ s/µm$^3$ for purely diffusive flux. For this device, a 1 M source imposes a net species flux of 4.1×10$^{-5}$ mol/hr/cm$^2$ into the cell culture well for a species with diffusivity 5.0×10$^{-6}$ cm$^2$/s.

The device design is quite flexible, allowing for numerous variations in both membrane and microfluidic parameters. When considering new designs, an analytical model is able to quickly determine delivery properties. Models can also be used to direct device designs based on prescribed deliveries. An electrical analogue where each geometrical device feature contributes a diffusive resistance to the total device resistance was used as the basis for the analytical delivery model.[29] Since the flux through the membrane is approximately constant over experimental timescales, the analytical model can be simplified by assuming steady state diffusion (FIG. 5D). Equation 1 defines the diffusion resistance from the flow channel into the culture well, $$R_T = \alpha R_B + \frac{R_d + R_c}{N} = \frac{4\phi\alpha Nr^2 + L(\pi r + 4l)}{4NDL\pi r^2}$$

where $R_T$ is the total device resistance (s/µm$^3$), $R_d$ is the resistance of a cylindrical pore, $R_c$ is the resistance of the pore exit, modeled as a Weber's Disc, and $R_B$ is a pore density dependant resistance figure which accounts for the flux from one nanopore over the microfluidic channel influencing neighboring nanopores[30].

Figure 5E:
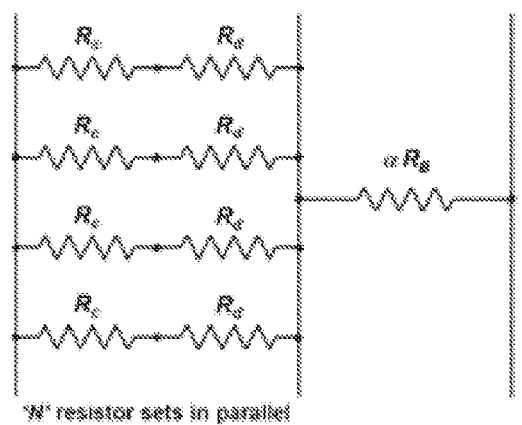
FIG. 5E illustrates an electrical resistance model is used for diffusive resistance. The diffusive resistance of a pore, $R_c$, is in series with the resistance of the pore exit, Rd. N of these branches are wired in parallel, where N is the total number of pores. This is in turn wired with RB and a, which accounts for the variation in concentration at the pore surfaces. The total resistance of this circuit is $R_T$. The units for diffusive resistance are $s/\mu m^3$.

The model for $R_B$ uses conformal transformations detailed by Saito[31] and assumes constant concentration boundary conditions, whereas the finite element simulation assumes zero-flux boundaries. In $R_B$, the channel length is L and ϕ is a proportionality constant that accounts for the fixed concentration boundary and has a value of approximately 5.3. This solution is independent of channel width, although channel width is indirectly taken into account through N, the total number of nanopores connecting the flow channel to the culture well. The remaining terms are geometric parameters: r is the pore radius, l is the membrane thickness, D is the diffusivity of the species, and a is a device specific adjustment factor to account for variations in surface concentration across the channel width. For this design, a data fit shows a to be 2.5, which predicts a flux in excellent agreement with the empirical data shown in FIG. 5D. The device elements are shown in FIG. 5E as a resistor circuit. In the electrical-diffusion analogue, current is equated to molecular flux J, voltage is equated to concentration difference $\Delta\phi$, and both are related by Ohm's Law, $J=\Delta\phi/R$. The analytical models indicate that the device flux is directly proportional only to D, as $R_T$ scales with 1/D. However, increasing device parameters N, r, or L causes the flux to increase, while increasing/causes the flux to decrease.

Chemical Gradients

Figures 5F, 5G, 5H:
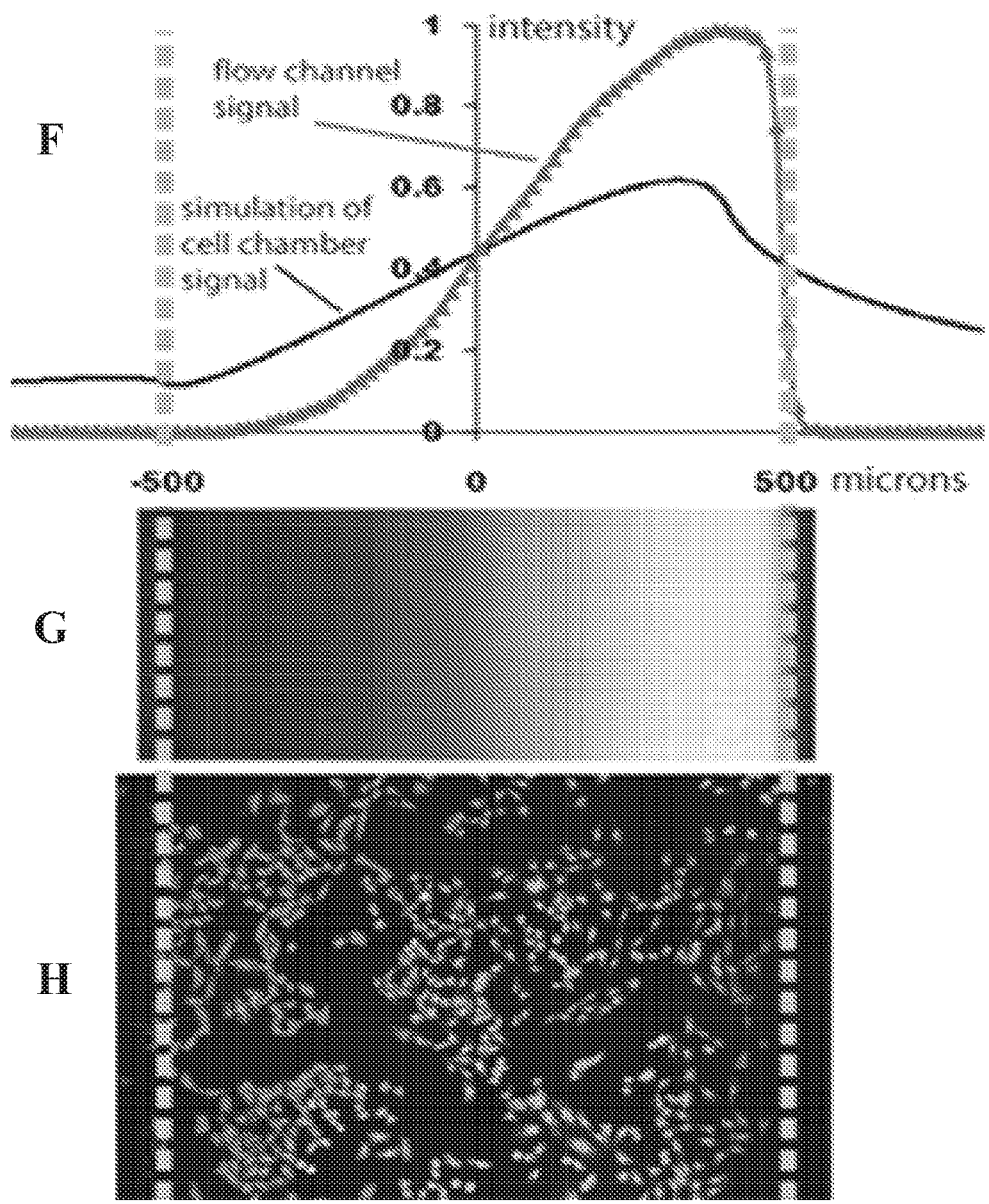
FIG. 5F illustrates an intensity profile, in triangles, of FIG. 5G.
FIG. 5G shows the fluorescent channel cross section of a dye gradient in a 1000 µm channel between water and Oregon Green fluorescent inputs.
FIG. 5H illustrates a composite fluorescent image of dyed cells from contrasting gradients in the main flow channel, ethidium homodimer, and SYBR Green I, demonstrates the cell chamber gradient.

As a representative signal pattern, a lateral gradient was created across the main device channel. The gradient is shown in FIGS. 5F and 5G where one input is fluorescently labeled with Oregon Green dye, and the other input is DI water. The signal intensity within the channel is well-described by a sigmoid function, which accounts for wall effects. Since the delivery through the membrane is based on the chemical composition in the channel, a wide range of gradients are possible using previously reported devices.[32] However, the membrane acts to smooth out the original signal, degrading both spatial and temporal signal fidelity. In FIG. 5F, the delivered signal has a lower peak, higher minimum, and shallower gradient compared to that of the original signal, and the peak maximum is shifted from the channel edge to approximately 85% of the channel width. Additionally, while the signal in the channel is static, the signal in the cell culture well will slowly increase as signal is accumulated. This effect is quite slow, with a few percent change occurring over the course of days. The increase in background signal intensity can be reduced further simply by creating a larger cell culture chamber, or by introducing sinks Delivery to Cells To demonstrate diffusive delivery of chemical species in a lateral gradient, CHO cells were cultured on a polycarbonate membrane, fixed in 70% methanol and stained with contrasting DNA-specific stain gradients. A 1000 μm flow channel was centered under a 1 cm×1 cm cell culture area and a lateral gradient was imposed using a flow rate of 2 μl/min for 10 minutes. Fluorescent imaging shows the CHO cells stained on the membrane over the device channel in FIG. 5H. The flow channel gradient is translated to a cell chamber gradient as described previously, with maximum intensity slightly inward from the channel edge.

Temporally Variant Signal Generation

In addition to creating static signal gradients, the microdevices can also produce temporally variant signals by altering the microfluidic inputs.

Figures 5I, 5J, 5K, 5L:
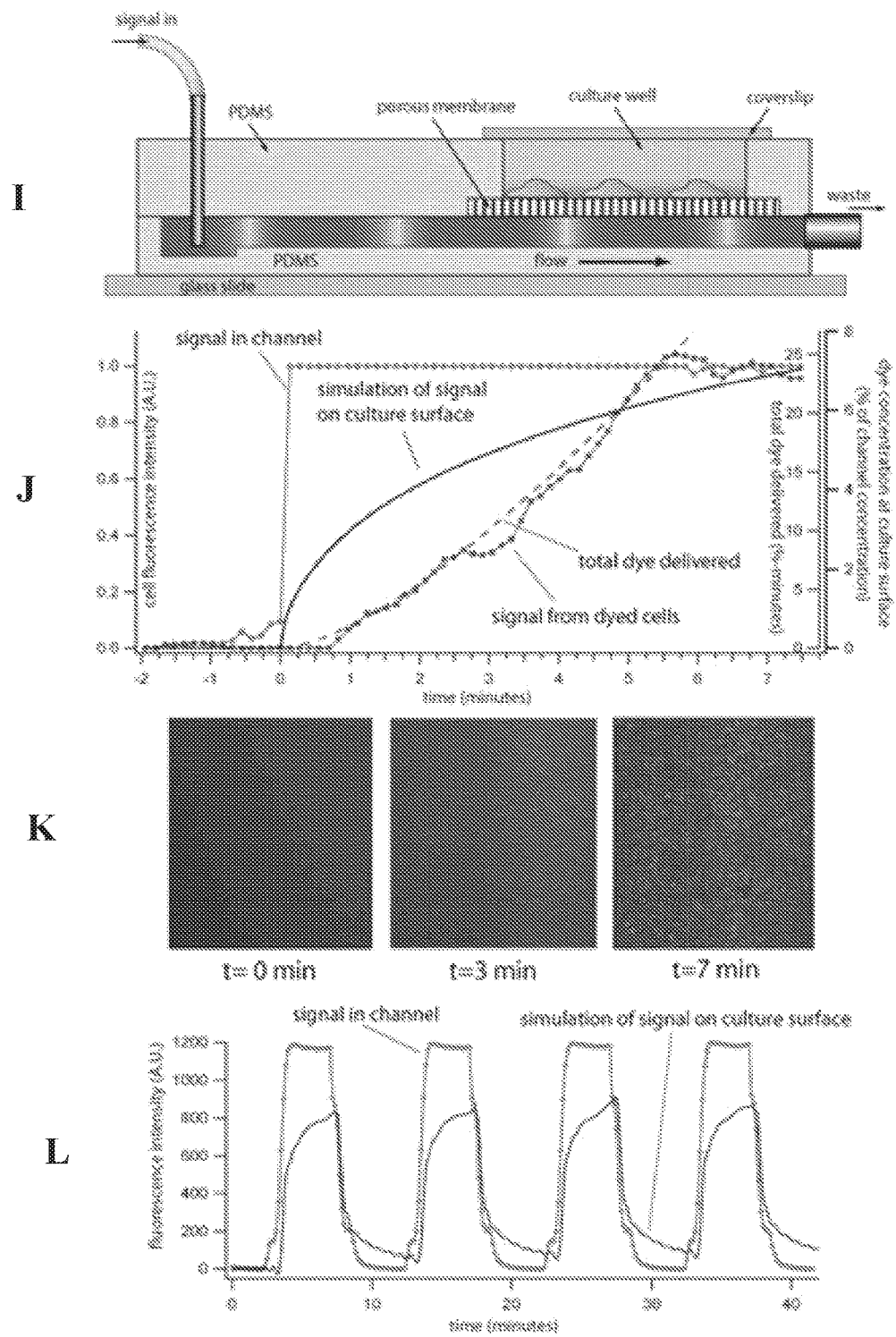
FIG. 5I illustrates alternating between buffer and fluorescent inputs produces temporally variant signal patterns.
FIG. 5J illustrates the step function onset of a 1000 μm wide gradient in the channel is indicated by a sharp DAPI fluorescence increase (diamonds). The stain diffuses across the membrane quickly, reaching one percent of the channel concentration in 8 seconds (trace, outside-right axis), and begins measurably staining cells 45 seconds after signal turn-on, with cells becoming fully stained in under six minutes (squares). The increase in cellular fluorescence follows the increase in total delivered dye (dashed trace, inside-right axis), which is the integral of the culture surface dye concentration (trace).
FIG. 5K illustrates fluorescent micrographs show the evolution of the stained cells. Image width is 1000 μm.
FIG. 5L illustrates five minute pulses at 5 psi produce a square signal pattern in the fluidic channel. The curve is a FEM simulation of this signal on the membrane cell culture surface.

The signal delivery rate to cells was quantified by monitoring the staining of fixed CHO cells with the step function delivery of a gradient of two different color DNA-labeling dyes (FIGS. 5J and 5K). The signal from a DAPI indicator dye within the underlying channel sharply increased as the DNA dye gradient was introduced (FIG. 5J, red diamonds). Cell staining over the entire gradient width (1000 μm) is first evident 45 seconds after signal turn-on, (FIG. 5J, green trace) demonstrating diffusive delivery of a large area gradient in under a minute. This is much faster than similar technologies, which can require hours to diffusively generate comparable sized gradients.[20]

After cell staining begins, the cell fluorescent signal increases linearly until reaching a plateau after 5.5 minutes. This is an extremely rapid introduction of a diffusive chemical gradient compared to the time to establish a similar gradient using lateral diffusion from the edges, which would take on the order of 40 hours to equilibrate across the width of this device (1.7 cm). Although cell staining is first evident in 45 seconds and constant by 5.5 min, the actual delivery of the dye to the cell surface is certainly faster, as these rates includes the time for the dye to migrate into the cell nucleus and bind to DNA. An FEM simulation of the dye concentration at the cell culture surface, normalized to the channel concentration, is shown in FIG. 5K (blue trace). According to the simulation, it takes only ~8 seconds after signal turn-on for the culture surface dye concentration to reach 1% of the channel concentration. The simulated dye delivery sum is in excellent agreement with the observed cell fluorescence (which reflects the integrated exposure to the dye) as shown in FIG. 5J (magenta trace). This also demonstrates linear accumulation of the chemical species within the cell as a function of the chemical concentration at the membrane surface, as would be expected for cell-permeant dyes. The total amount of dye delivered to the cells before the cell fluorescence plateaus is equal to the amount delivered during the recommended dye staining protocol, confirming that the plateau is caused by dye saturation of the cells.

Pulsed chemical delivery was also possible. Square-wave chemical pulses were introduced using a computer controlled 5 psi gaseous pressure source, and alternating the pressure supply between buffer and fluorescent inputs (FIG. 5L). The signal pulses shown here are five minutes in length, but could be shortened through device alterations. The translation of a transient signal pattern in the flow channel to the cell culture surface is also simulated (FIG. 5L, blue trace). Using an 8 term Fourier series to approximate the square signal input, FEM simulation shows that both the increasing and decreasing signal is delivered in under a minute with some loss to the signal intensity and fidelity through a 10 um thick membrane with a porosity of 5%. The shoulders in the channel signal patterns are due to mixing and backflow between the signal and blank input lines during periods when only one flow line is pressurized. These could be eliminated with valves in the microfluidic channels.

Conclusions

A large-area, diffusive delivery, microfluidic system is presented. By using a nanoporous membrane to separate the flow channels and culture well, this design allows for chemical signals in the microfluidic channels to diffuse to the cells in culture. The cells are exposed to the microfluidic signals, but without fluid flow and its accompanying shear forces and perturbations. This novel concept allows for the use of active microfluidic devices and all the control options they offer, without the complications that arise from fluid flow. Further studies enabled by this new microfluidic method have the potential to mimic in vivo cellular environments in increasingly complex and biologically relevant ways.

REFERENCES each of which is incorporated herein by reference

1. Scadden, D. T., The stem-cell niche as an entity of action. Nature, 2006. 441(7097): p. 1075-1079.
2. Lutolf, M. P. and J. A. Hubbell, Synthetic biomaterials as instructive extracellular microenvironments for morphogenesis in tissue engineering. Nat. Biotechnol., 2005. 23(1): p. 47-55.
3. Yu, H., et al., Diffusion dependent cell behavior in microenvironments. Lab Chip, 2005. 5(10): p. 1089-1095.

4. Giancotti, F. G. and E. Ruoslahti, Transduction—Integrin signaling. Science, 1999. 285(5430): p. 1028-1032.
5. Engler, A. J., et al., Matrix elasticity directs stem cell lineage specification. Cell, 2006. 126(4): p. 677-689.
6. Alberts, B., et al., Molecular Biology of the Cell. 4th ed. 2002, New York, N.Y.: Garland Science.
7. Geldof, A. A., Nerve-Growth-Factor-Dependent Neurite Outgrowth Assay—A Research Model for Chemotherapy-Induced Neuropathy. J. Cancer Res. Clin. Oncol., 1995. 121(11): p. 657-660.
8. Whitesides, G. M., The origins and the future of microfluidics. Nature, 2006. 442(7101): p. 368-73.
9. Keenan, T. M. and A. Folch, Biomolecular gradients in cell culture systems. Lab Chip, 2008. 8(1): p. 34-57.
10. Sakiyama-Elbert, S. E., Controlled release of nerve growth factor from a heparin-containing fibrin-based cell ingrowth matrix. J. Controlled Release, 2000. 69(1): p. 149-158.
11. Lee, K. Y. and D. J. Mooney, Hydrogels for tissue engineering. Chemical Reviews, 2001. 101(7): p. 1869-1879.
12. Uhrich, K. E., et al., Polymeric systems for controlled drug release. Chem. Rev., 1999. 99(11): p. 3181-3198.
13. Patel, N., et al., Spatially controlled cell engineering on biodegradable polymer surfaces. FASEB J., 1998. 12(14): p. 1447-1454.
14. Griffith, L. G., Polymeric biomaterials. Acta Mater., 2000. 48(1): p. 263-277.
15. Walker, G. M., et al., Effects of flow and diffusion on chemotaxis studies in a microfabricated gradient generator. Lab Chip, 2005. 5(6): p. 611-618.
16. Wang, H., et al., Shear stress induces endothelial differentiation from a murine embryonic mesenchymal progenitor cell line. Arterioscler., Thromb., Vasc. Biol., 2005. 25(9): p. 1817-1823.
17. Langille, B. L. and S. L. Adamson, Relationship Between Blood Flow Direction and Endothelial Cell Orientation at Arterial Branch Site in Rabbits and Mice. Circ. Res., 1981. 48(4): p. 481-488.
18. Bancroft, G. N., et al., Fluid flow increases mineralized matrix deposition in 3D perfusion culture of marrow stromal osteoblasts in a dose-dependent manner. Proc. Natl. Acad. Sci. U.S. A, 2002. 99(20): p. 12600-12605.
19. Shamloo, A., et al., Endothelial cell polarization and chemotaxis in a microfluidic device. Lab Chip, 2008. 8(8): p. 1292-1299.
20. Abhyankar, V. V., et al., Characterization of a membrane-based gradient generator for use in cell-signaling studies. Lab Chip, 2006. 6(3): p. 389-393.
21. Diao, J., et al., A three-channel microfluidic device for generating static linear gradients and its application to the quantitative analysis of bacterial chemotaxis. Lab Chip, 2006. 6: p. 381-88.
22. Keenan, T. M., C. H. Hsu, and A. Folch, Microfluidic "jets" for generating steady-state gradients of soluble molecules on open surfaces. Appl. Phys. Lett., 2006. 89(11).
23. Wu, H., B. Huang, and R. N. Zare, Generation of complex, static solution gradients in microfluidic channels. J. Am. Chem. Soc., 2006. 128(13): p. 4194-95.
24. Boyden, S. V., The chemotactic effect of mixtures of antibody and antigen on polymorphonuclear leucocytes. J. Exp. Med., 1962. 115(3): p. 453-66.
25. Zicha, D., G. A. Dunn, and A. F. Brown, A new direct-viewing chemotaxis chamber. J. Cell Sci., 1991. 99: p. 769-75.
26. Zigmond, S. H., Orientation chamber in chemotaxis. Methods Enzymol., 1988. 162: p. 65-72.
27. Ainslie K A, L. R., Beaudette T T, Petty L, Bachelder E M, and Desai T A, Microfabricated Devices for Enhanced Bioadhesive Drug Delivery: Attachment to and Small Molecule Release through a Cell Monolayer under Flow. Small, 2009. 5(24): p. 2857-2863.
28. Jeon, N. L., et al., Generation of solution and surface gradients using microfluidic systems. Langmuir, 2000. 16(22): p. 8311-8316.
29. Berg, H. C., Random Walks in Biology. Rev. Ed. ed. 1993, Princeton, N.J.: Princeton University Press. 152.
30. Crank, J., The Mathematics of Diffusion. 2nd ed. 1975, Oxford.
31. Saito, Y., A Theoretical Study on the Diffusion Current at the Stationary Electrodes of Circular and Narrow Band Types. Rev. Polarography (Japan), 1968. 15(6): p. 177-187.
32. Dertinger, S. K. W., et al., Generation of gradients having complex shapes using microfluidic networks. Anal. Chem., 2001. 73(6): p. 1240-1246.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to units and measuring techniques corresponding to the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:
1. A nanotube device, comprising:
a porous structure having a pore diameter and a plurality of nanotubes extending through the porous structure, wherein the nanotubes extend a distance above the porous structure of between 2 nm and 50 μm and are hollow to allow material to pass through the nanotubes and have an inner diameter of between 5 nm-700 nm wherein the nanotubes of the porous structure are in fluidic communication with a fluidic passage of a device on the side opposite the nanotubes extending from the surface of the porous structure;
further wherein the density of the nanotubes is greater than about $10^6$ nanotubes/cm$^2$.
2. The nanotube device of claim 1, further comprising a layer of material disposed on the bottom of the porous structure on the side opposite the nanotubes extending from the surface of the porous structure, wherein the material of the layer and the nanotubes are made of the same material.

3. The nanotube device of claim 1, further comprising a holding structure, wherein the porous structure is the bottom surface of the holding structure, wherein walls form the side boundaries of the holding structure, and wherein the nanotubes extending above the porous structure surface extend up into the area bounded by the walls and the porous structure.

4. The nanotube device of claim 1, wherein the porous structure is made of a material that is different than the nanotubes.

5. The nanotube device of claim 1, wherein the distance above the porous structure that the nanotubes extend is between 100 nm to 10 μm.

6. The nanotube device of claim 1, wherein the porous structure is made of a material selected from the group consisting of: polycarbonate, polyester, a polymer, an etchable material that can be processed with pores, silicon, and a combination thereof.

7. The nanotube device of claim 1, wherein the nanotubes are made of a material selected from the group consisting of: alumina, $TiO_2$, $SnO_2$, $ZrO_2$, $ZnO_2$, carbon, a nitride, platinum, gold, silver, indium tin oxide (ITO), $SiO_2$, Ni, NiO, and a combination thereof.

8. The nanotube device of claim 1, wherein the porous structure has a thickness of between 100 nm to 50 μm.

9. The nanotube device of claim 1, further wherein the fluidic passage is configured for rapid fluid exchange as compared to flow through the nanotubes.

10. A nanotube device, the device comprising:
a porous structure and a plurality of nanotubes extending through the porous structure and extending a distance above the porous structure of between 2 nm to 50 μm, at a density of between about $10^6$ and $10^8$ nanotubes/$cm^2$, wherein the nanotubes have a wall thickness of between 5-500 nm;
a fluidic passage on a side of the porous structure opposite from a side the nanotubes extending above the porous structure, wherein the nanotubes are in fluidic communication with the fluidic passage so that a material can pass between the fluidic passage through the nanotubes.

11. The device of claim 10, further comprising a layer of material disposed on the bottom of the porous structure on the side opposite the nanotubes extending from the surface of the porous structure, wherein the material of the layer and the nanotubes are made of the same material.

12. The device of claim 11, wherein the fluidic passage comprises a microfluidic device.

13. The device of claim 11, further comprising a holding structure, wherein the porous structure is the bottom surface of the holding structure, wherein walls form the side boundaries of the holding structure, and wherein the nanotubes extending above the porous structure surface extend up into the area bounded by the walls and the porous structure.

14. The device of claim 11, wherein the porous structure is made of a material that is different than the nanotubes.

15. The device of claim 11, wherein the distance above the porous structure is between 100 nm to 10 μm.

16. The device of claim 11, wherein the porous structure is made of a material selected from the group consisting of: polycarbonate, polyester, a polymer, an etchable material that can be processed with pores, silicon, and a combination thereof.

17. The device of claim 11, wherein the nanotubes are made of a material selected from the group consisting of: alumina, $TiO_2$, $SnO_2$, $ZrO_2$, $ZnO_2$, carbon, a nitride, platinum, gold, silver, indium tin oxide (ITO), $SiO_2$, Ni, NiO, and a combination thereof.

18. The device of claim 11, wherein the porous structure has a thickness of about 100 nm to 50 μm.

* * * * *

UNITED STATES PATENT AND TRADEMARK OFFICE
CERTIFICATE OF CORRECTION

PATENT NO. : 10,150,947 B2
APPLICATION NO. : 14/991853
DATED : December 11, 2018
INVENTOR(S) : Jules J. Vandersarl et al.

It is certified that error appears in the above-identified patent and that said Letters Patent is hereby corrected as shown below:

In the Specification

Column 1, Lines 27-30 following STATEMENT REGARDING FEDERALLY SPONSORED RESEARCH OR DEVELOPMENT:
Please delete: "This invention was made with Government support under contract DE-AC02-76-SF00515 awarded by the Department of Energy. The Government has certain rights in the invention."
And insert: --This invention was made with Government support under contract DE-AC02-76SF00515 awarded by the Department of Energy. The Government has certain rights in the invention.--

Signed and Sealed this
Twenty-first Day of May, 2024

Katherine Kelly Vidal
*Director of the United States Patent and Trademark Office*